(12) United States Patent
Myers et al.

(10) Patent No.: US 12,318,326 B2
(45) Date of Patent: *Jun. 3, 2025

(54) COOLING SYSTEM AND METHOD FOR A PROSTHETIC SOCKET

(71) Applicant: Vivonics, Inc., Bedford, MA (US)

(72) Inventors: Ryan Myers, North Andover, MA (US); Kristen LeRoy, Waltham, MA (US); Ian Cohen, Boulder, CO (US); Gordon B. Hirschman, Cohoes, NY (US); Thane R. Hunt, Colchester, CT (US); Kevin E. Keough, Sharon, MA (US); Carlos Martinez Luna, Boylston, MA (US); Todd R. Farrell, Waltham, MA (US); Jennifer L. Johansson, Wayland, MA (US); Brendan LaBrecque, Middleton, MA (US)

(73) Assignees: Vivonics, Inc., Bedford, MA (US); Liberating Technologies, Inc., Holliston, MA (US)

( * ) Notice: Subject to any disclaimer, the term of this patent is extended or adjusted under 35 U.S.C. 154(b) by 454 days.

This patent is subject to a terminal disclaimer.

(21) Appl. No.: 17/748,581

(22) Filed: May 19, 2022

(65) Prior Publication Data

US 2022/0273488 A1     Sep. 1, 2022

Related U.S. Application Data

(63) Continuation of application No. 16/211,974, filed on Dec. 6, 2018, now Pat. No. 11,364,142, which is a
(Continued)

(51) Int. Cl.
*A61F 7/00*     (2006.01)
*A61F 2/60*     (2006.01)
(Continued)

(52) U.S. Cl.
CPC .................. *A61F 7/00* (2013.01); *A61F 2/60* (2013.01); *A61F 2/7812* (2013.01); *A61F 2/80* (2013.01);
(Continued)

(58) Field of Classification Search
CPC .. A61F 2/60; A61F 2/68; A61F 2/7812; A61F 2/80; A61F 2002/7665; A61F 7/10;
(Continued)

(56) References Cited

U.S. PATENT DOCUMENTS 6,003,591 A    12/1999  Campbell
6,010,528 A *   1/2000  Augustine ................. A61F 7/02
                                                   607/104
(Continued)

FOREIGN PATENT DOCUMENTS

WO       2017004540 A1     1/2017

OTHER PUBLICATIONS

WillowWood, "A Successful Collaboration To Improve Transfemoral Sockets", Apr. 1, 2015, "https://www.willowwoodco.com/news-events/", two (2) pages.
(Continued)

*Primary Examiner* — Christie Bahena
(74) *Attorney, Agent, or Firm* — Iandiorio Teska & Coleman, LLP

(57) ABSTRACT

A prosthetic socket cooling system and method includes a thermally conductive heat spreader including a curved shaped portion configured to maximize contact with a residual limb of a user. A heat extraction subsystem is coupled through a wall of the prosthetic socket and to the thermally conductive heat spreader and is configured to maintain a desired temperature inside the prosthetic socket.

50 Claims, 34 Drawing Sheets

Related U.S. Application Data continuation-in-part of application No. 15/590,679, filed on May 9, 2017, now abandoned.

(60) Provisional application No. 62/334,758, filed on May 11, 2016.

(51) Int. Cl.
| | |
|---|---|
| *A61F 2/78* | (2006.01) |
| *A61F 2/80* | (2006.01) |
| *A61F 7/02* | (2006.01) |
| *H10N 10/13* | (2023.01) |
| *A61F 5/01* | (2006.01) |

(52) U.S. Cl.
CPC ................ *H10N 10/13* (2023.02); *A61F 5/01* (2013.01); *A61F 2007/0051* (2013.01); *A61F 2007/0067* (2013.01); *A61F 2007/0075* (2013.01); *A61F 2007/0078* (2013.01); *A61F 2007/0093* (2013.01); *A61F 2007/0095* (2013.01); *A61F 2007/0096* (2013.01); *A61F 2007/0228* (2013.01); *A61F 2007/0246* (2013.01); *A61F 2007/0247* (2013.01); *F28F 2230/00* (2013.01); *F28F 2255/00* (2013.01)

(58) Field of Classification Search
CPC ...... A61F 2007/0041; A61F 2007/0051; A61F 2007/0067; A61F 2007/0075; A61F 2007/0078; A61F 2007/0093; A61F 2007/0095; A61F 2007/0096; A61F 2007/0228; A61F 2007/0246; A61F 2007/0247; A61F 5/01; F28L 2230/00; F28F 2255/00

See application file for complete search history.

(56) References Cited

U.S. PATENT DOCUMENTS

| | | |
|---|---|---|
| 6,123,716 A | 9/2000 | Augustine et al. |
| 6,224,623 B1 | 5/2001 | Augustine et al. |
| 9,358,138 B2 | 6/2016 | Kelley et al. |
| 9,814,607 B2 | 11/2017 | Zhe et al. |
| 2011/0197598 A1 | 8/2011 | Cheng et al. |
| 2013/0079893 A1 | 3/2013 | Allemand |
| 2014/0025183 A1 | 1/2014 | Kelley et al. |
| 2014/0309750 A1 | 10/2014 | Kelley et al. |
| 2015/0105865 A1 | 4/2015 | Davis et al. |
| 2015/0238330 A1 | 8/2015 | Jonsson et al. |
| 2016/0030207 A1* | 2/2016 | Walters, Jr. ............... A61F 2/80 623/33 |
| 2016/0081822 A1 | 3/2016 | Zhe et al. |
| 2019/0099286 A1 | 4/2019 | Myers et al. |

OTHER PUBLICATIONS

LetoSolutions™, "The Aquilonix™ Prosthesis Cooling System", Mar. 16, 2017, "http://www.letosolutions.net/our-solution.html", two (2) pages.

Assistive Technology, The Official Journal of RESNA, "Temperature Measurement and Control System For Transtibial Prostheses: Functional Evaluation", 30, 1, 2018, pp. 16-23 plus cover sheet.

\* cited by examiner

FIG. 3

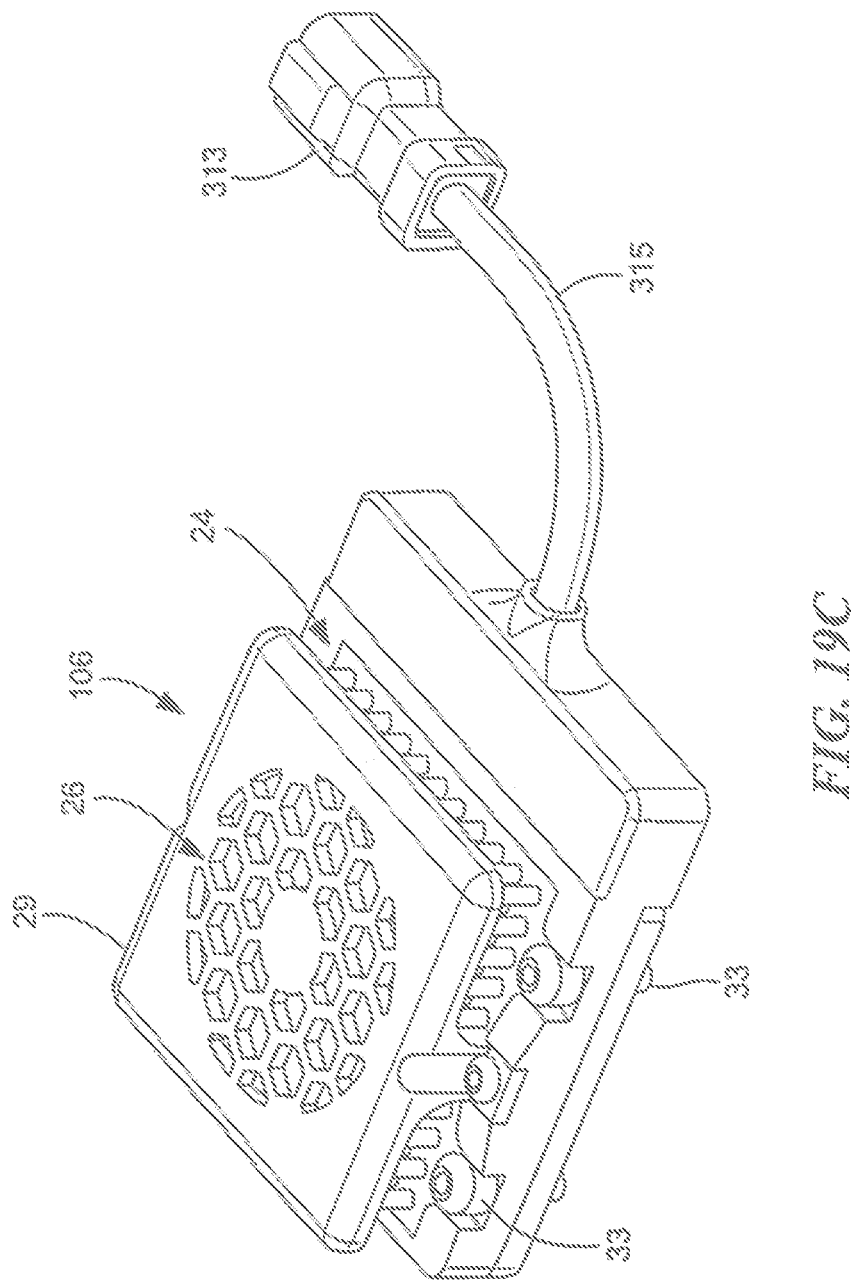

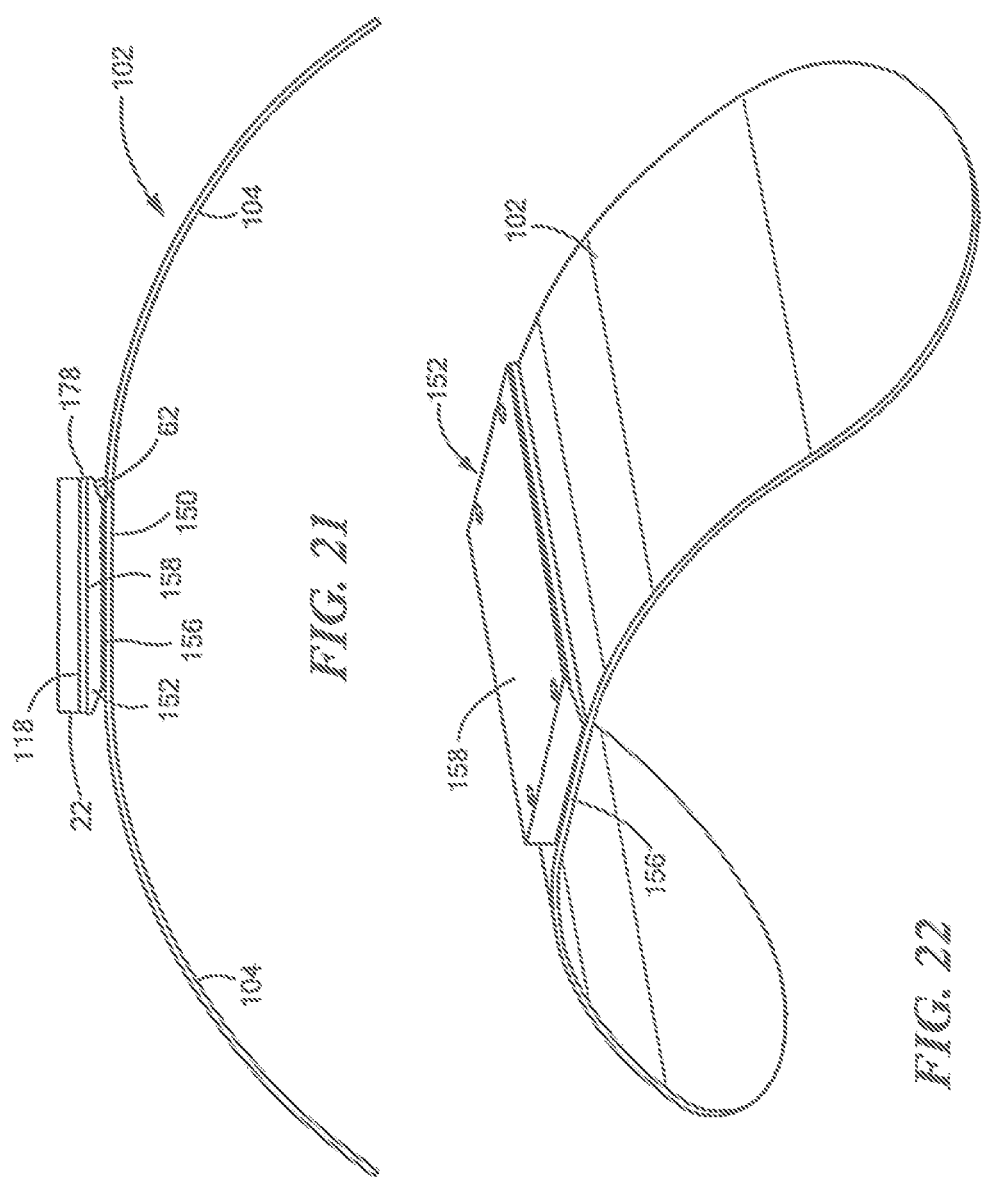

COOLING SYSTEM AND METHOD FOR A PROSTHETIC SOCKET

RELATED APPLICATIONS

This application claims benefit and priority to U.S. patent application Ser. No. 16/211,974 filed Dec. 6, 2018, under 35 U.S.C. §§ 119, 120, 363, 365, and 37 C.F.R. § 1.55 and § 1.78, and that and this application claim benefit and priority to U.S. patent application Ser. No. 15/590,679 filed May 9, 2017, under 35 U.S.C. §§ 119, 120, 363, 365, and 37 C.F.R. § 1.55 and § 1.78, which hereby claims the benefit of and priority thereto U.S. Provisional Application Ser. No. 62/334,758 filed May 11, 2016, under 35 U.S.C. §§ 119, 120, 363, 365, and 37 C.F.R. § 1.55 and § 1.78, which is incorporated herein by this reference.

GOVERNMENT RIGHTS

This invention was made with government support under W81XWH-13-1-0453 and W81XWH-17-C-0005 awarded by the U.S. Army. The government has certain rights in the invention.

FIELD OF THE INVENTION

This invention relates to a cooling system and method for a prosthetic socket.

BACKGROUND OF THE INVENTION

Nearly 2 million people are living with limb loss in the United States. A significant portion of both civilians and soldiers who undergo amputation are now being fitted with state of the art prosthetic devices. Improvements in prosthetic limb function have outpaced improvements to the comfort of the devices. Prosthetic sockets typically include a hard outer shell that functions as a mechanical interface between the residual limb and prosthetic limb, e.g., a foot, a hand, and the like. A silicone liner up to about 1 cm thick may be worn over the residual limb for cushioning and to improve connection to the prosthesis. Layers of socks may also be worn over the liner to maintain socket fit as the limb experiences natural changes in residual limb volume. Heat and moisture trapped by these non-breathable and thermally insulating materials may create a warm, moist, and adverse environment.

The trapped heat and perspiration may lead to potential skin problems of the residual limb such as folliculitis, friction blisters, bacterial growth, and the like. In one survey of transfemoral amputees, heat and perspiration inside the socket was reported by 72% of the survey participants as the most common cause for a reduced quality of life. Similarly, poorly managed moisture at the interface between the residual limb and the inner prosthetic socket and/or liner may lead to skin irritation and infections which may decrease the usability of the prosthesis. Elevated temperatures in the prosthetic socket may also lead to increased sweating and friction, skin damage, discomfort, and reduced quality of life.

Studies have found increases in socket temperature for a period as short as 10 minutes of walking after the prosthesis was donned. It was also found that temperatures remained elevated long after activity cessation. Even a rest period greatly exceeding the duration of the preceding activity period may be insufficient to return the limb to its initial temperature. Studies also suggest that a modest temperature increase of only 2° C. may be responsible for reports of thermal discomfort by amputees. Therefore, a small amount of activity may cause the socket temperature to elevate and remain at an uncomfortable level for an extended period of time which may lead to decreased wear times.

In summary, an uncomfortable or non-performing socket/residual limb interface due to temperature increase in the socket may decrease prosthesis use among amputees who want to remain active in their civilian and military lives.

Several prior publications propose prosthetic cooling systems integrated with the prosthetic socket. See, for example, U.S. Patent Publication 2016/0030207; U.S. Pat. No. 9,358,138; U.S. 2015/0105865; US 2016/0030207; U.S. Pat. No. 6,123,716; and WO 2017/004540 all incorporated herein by this reference.

SUMMARY OF THE INVENTION

In one aspect, a prosthetic socket cooling system is featured. The system includes a thermally conductive heat spreader including a curved shaped portion configured to maximize contact with a residual limb of a user. A heat extraction subsystem coupled through a wall of the prosthetic socket and to the thermally conductive heat spreader is configured to maintain a desired temperature inside the prosthetic socket.

In one embodiment, the thermally conductive heat spreader and the heat extraction subsystem may be positioned at a mid-location of the prosthetic socket or positioned at an upper-location of the prosthetic socket. The heat extraction subsystem may include a thermal electric cooler (TEC) having a predetermined shape and a flat surface having a predetermined surface area. The heat extraction subsystem may include a heat sink coupled to the TEC and a fan positioned to urge air over the heat sink. The system may include a thermally conductive adapter coupled between the thermally conductive heat spreader and the heat extraction subsystem. The thermally conductive adapter may include a curved surface on one side configured to approximately match the curved shaped portion of the thermally conductive heat spreader and a predetermined shape and flat surface on the other side configured to approximately match the predetermined shape and the flat surface and predetermined surface area of the TEC. The thermally conductive heat spreader may include a flat portion. The thermally conductive adapter may include a flat surface on one side configured to approximately match the flat portion of the thermally conductive heat spreader and a flat surface on the other side and configured to approximately match the predetermined shape, flat surface, and predetermined surface area of the TEC. The flat surface on the side configured to approximately match the flat portion of the thermally conductive heat spreader may be sized to conform to the residual limb of the user. The thermally conductive heat spreader may be sized to maximize performance of the TEC. The system may include a thermally conductive spacer coupled between the thermally conductive adapter and the TEC. The fan may be configured to urge the air in a downward direction from the prosthetic socket towards a foot of the user. The system may include a conduit coupled to the fan configured to direct the air in the downward direction. The system may include flexible bellows coupled to the fan configured to direct the air in a downward direction. The system may include a protective housing coupled to the prosthetic socket configured to allow the fan to direct the air in the downward direction when a suspension sleeve placed over the residual limb and the prosthetic socket. The heat extraction subsystem may include a user interface, an electronic section, one or more temperature sensors, one or more accelerometers, and a power supply. The system may include a housing about the fan, the TEC, the heat sink, the user interface, the electronics section, and the battery. The electronics section may include a controller subsystem. The controller subsystem may be configured to operate the TEC based and/or the fan based on signals from the user interface and/or the one or more temperature sensors and/or the one or more accelerometers. The controller subsystem and the one or more temperature sensors may be configured to measure and/or estimate skin temperature of the residual limb of the user and adjust a cooling temperature of the TEC based on the measured or estimated skin temperature and a predetermined set point temperature. The controller subsystem, the one or more temperature sensors, and/or the one or more accelerometers may be configured to measure and/or estimate one or more of: a skin temperature of the residual limb of the user, a temperature of a hot-side of the TEC, a temperature of a cold-side of the TEC, an ambient temperature, and motion activity of the user and the controller subsystem may be configured to adjust the temperature of the TEC such that a desired temperature is maintained inside the prosthetic socket based on one or more of the measured and/or estimated skin temperature, the temperature of the hot-side of the TEC, the cold-side of the TEC, the ambient temperature, the motion activity, and a predetermined set point temperature. The controller subsystem may be configured to adjust the temperature of the TEC such that a desired temperature inside the prosthetic socket is maintained based on a temperature set point provided by the user. The controller subsystem, the one or more temperature sensors, and/or the one or more accelerometers may be configured to measure and/or estimate one or more of: a skin temperature of the residual limb of the user, a temperature of a hot-side of the TEC, a temperature of a cold-side of the TEC, an ambient temperature, and motion activity of the user and the controller subsystem is configured to adjust the temperature the TEC such that a desired temperature inside the prosthetic socket is maintained based on one of more of the measured and/or estimated skin temperature, the temperature of the hot-side and the cold-side of the TEC, the ambient temperature, the motion activity, and a temperature set point provided by the user. The controller subsystem may be configured to activate the TEC for a first predetermined duration of time and not activate the TEC for a second predetermined duration of time based on a set point provided by the user such that the desired temperature inside the prosthetic socket is maintained. The controller subsystem, the one or more temperature sensors, and the one or more accelerometers may be configured to determine an ambient temperature, a temperature of a hot-side of the TEC, a temperature of a cold-side of the TEC, and motion activity of the user and the controller subsystem may be configured to activate the TEC for a first predetermined duration of time and not activate the TEC for a second predetermined duration of time based on a set point provided by the user such that the desired temperature inside the prosthetic socket is maintained.

In another aspect, a prosthetic socket cooling system is featured. The system includes a thermally conductive heat spreader including a curved shaped portion configured to maximize contact with a residual limb of a user. A plurality of heat extraction subsystems are coupled through a wall of the prosthetic socket and to the thermally conductive heat spreader, the plurality of heat extraction subsystem sized to maximize contact with thermally conductive heat spreader.

In one embodiment, the thermally conductive heat spreader and the plurality of heat extraction subsystems may be positioned at a mid-location of the prosthetic socket or positioned at an upper-location of the prosthetic socket. Each of the plurality of heat extraction subsystems may include a thermal electric cooler (TEC). Each of the plurality of the heat extraction subsystems may include a heat sink coupled to the TEC and a fan positioned to urge air over the heat sink. The system may include one or more of: a user interface, an electronic section, one or more temperature sensors, one or more accelerometers, and a power supply. The electronics section may include a controller subsystem. The controller subsystem may be configured to operate each TEC and/or the fan based on signals from the user interface and/or the one or more temperature sensors and/or the one or more accelerometers. The controller subsystem and the one or more temperature sensors may be configured to measure and/or estimate one or more of: skin temperature of the residual limb of the use, a temperature of a hot-side of the TEC, a temperature of a cold-side of the TEC, and adjust a cooling temperature of the TEC based on one or more of the measured and/or estimated skin temperature, the temperature of the hot-side and the cold-side of the TEC, and a predetermined set point temperature. The controller subsystem, the one or more temperature sensors, and/or the one or more accelerometers may be configured to measure and/or estimate one or more of: a temperature of skin of the residual limb of the user, a temperature of a hot-side of the TEC, a temperature of a cold-side of the TEC, an ambient temperature, and motion activity of the user and the controller subsystem may be configured to adjust the temperature of the TEC such that a desired temperature is maintained inside the prosthetic socket based on the one or more of the measured and/or estimated skin temperature, the temperature of the hot-side, the temperature of the cold-side of the TEC, the ambient temperature, the motion activity, and a predetermined set point temperature. The controller subsystem may be configured to adjust the temperature of the TEC such that the desired temperature inside the prosthetic socket is maintained based on a temperature set point provided by the user. The controller subsystem, the one or more temperature sensors, and the one or more accelerometers may be configured to measure and/or estimate one or more of: a skin temperature of the residual limb of the user, a temperature of a hot-side of the TEC, a temperature of a cold-side of the TEC, an ambient temperature, and motion activity of the user and the controller subsystem may be configured to adjust the temperature the TEC such that the desired temperature inside the prosthetic socket is maintained based on one or more of the measured and/or estimated skin temperature, the temperature of the hot-side and the cold-side of the TEC, the ambient temperature, the motion activity, and a temperature set point provided by the user.

In another aspect, a method of cooling a prosthetic socket is featured. The method includes placing a thermally conductive heat spreader including a curved shape portion in contact with a residual limb of a user, placing a heat extraction subsystem through a wall of the prosthetic socket and coupling the heat extraction subsystem to the thermally conductive heat spreader, and operating the heat extraction subsystem to drive heat from inside the prosthetic socket to an external environment using the thermally conductive heat spreader and the heat extraction subsystem such that a desired temperature is maintained in the prosthetic socket.

In one embodiment, the method may include placing the thermally conductive heat spreader and the heat extraction subsystem at a mid-location of the prosthetic socket. The method may include placing the thermally conductive heat spreader and the heat extraction subsystem at an upper-location of the prosthetic socket. The method may include coupling a thermally conductive adapter between the thermally conductive heat spreader and the heat extraction subsystem. The method may include urging air in a downward direction from the prosthetic socket towards a foot of the user. The heat extraction subsystem may further include one or more of thermoelectric cooler (TEC), a user interface, an electronic section, one or more temperature sensors, one or more accelerometers, a fan, a heat sink, and a power supply. The method may include operating a TEC and/or the fan based on signals from a user interface and/or the one or more temperature sensors and/or the one or more accelerometers. The method may include measuring and/or estimating one or more of: a skin temperature of the residual limb of the user, a temperature of a hot-side of the TEC, a temperature of a cold-side of the TEC, and adjusting a cooling temperature of the TEC based on one or more of the measured and/or estimated skin temperature, the temperature of the hot-side and the cold-side of the TEC, and a predetermined set point temperature. The method may include measuring and/or estimating one or more of: a skin temperature of the residual limb of the user, a temperature of a hot-side of the TEC, a temperature of a cold-side of the TEC, an ambient temperature, and/or motion activity of the user and adjusting the temperature the TEC such that a desired temperature is maintained inside the prosthetic socket based on one or more of the measured and/or estimated skin temperature, the ambient temperature, the temperature of the hot-side of the TEC, temperature of the cold-side of the TEC, the motion activity, and the predetermined set point temperature. The method may include adjusting the temperature of the TEC such that the desired temperature inside the prosthetic socket is maintained based on a temperature set point provided by the user. The method may include measuring and/or estimating one or more of: a temperature of skin of the residual limb of the user, a temperature of a hot-side of the TEC, a temperature of a cold-side of the TEC, an ambient temperature, and motion activity of the user and adjusting the temperature the TEC such that the desired temperature inside the prosthetic socket is maintained based on one or more of the measured or estimated skin temperature, the temperature of the hot-side of the TEC, the temperature of the cold-side of the TEC, the ambient temperature, the motion activity, and temperature set point provided by the user.

In yet another aspect, a method of cooling a prosthetic socket is featured. The method includes providing a thermally conductive heat spreader including a curved shape portion in contact with a residual limb of a user, providing a plurality of heat extraction subsystems through a wall of the prosthetic socket and coupling the plurality of heat extraction subsystems to the thermally conductive heat spreader, and operating the plurality of heat extraction subsystems to drive heat from the prosthetic socket to an external environment via the thermally conductive heat spreader and the heat extraction subsystem to maintain a desired temperature inside the TEC.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 3 is a schematic view showing another example of a prosthetic socket cooling system;

FIGS. 19A, 19B, and 19C are schematic three-dimensional views showing in further detail one example of the primary components of the heat extraction subsystem shown in one or more of FIGS. 15-18B;

FIG. 21 is a schematic end-view showing in further detail the structure of the thermally conductive heat spreader and thermally conducive adapter shown in FIGS. 19A and 19B;

FIG. 22 is a schematic three-dimensional view of the thermally conductive heat spreader and the thermally conductive adapter shown in FIG. 21;

DETAILED DESCRIPTION OF THE INVENTION

Figure 1:
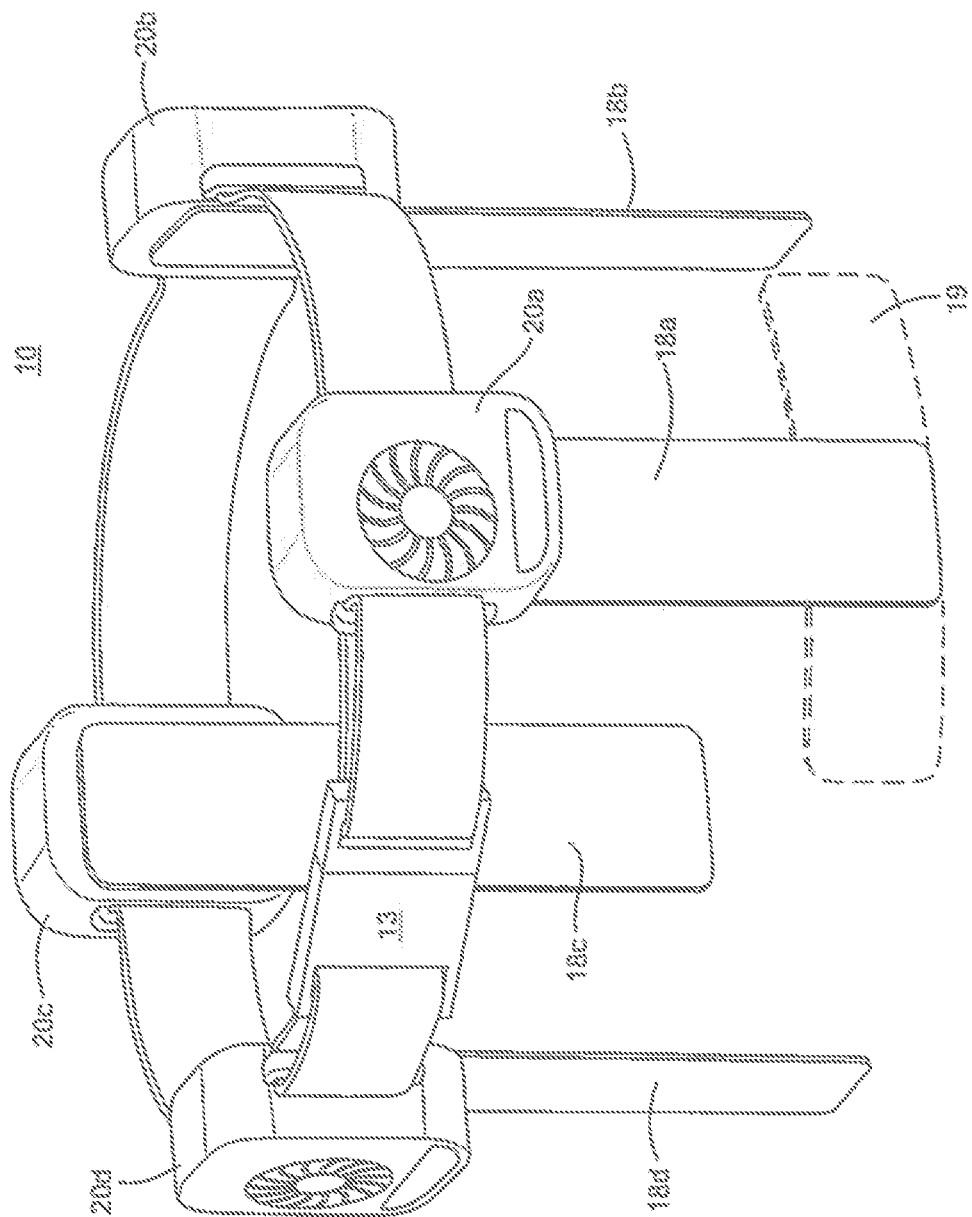
FIG. 1 is a schematic three-dimensional view showing one example of a prosthetic socket cooling system.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

A prosthetic socket cooling system in one or more embodiments of this invention is located alongside and/or within the prosthetic socket and allows the user to control the temperature within the socket and the residual limb to effectively reduce or eliminate the problems associated with the elevated temperature in the prosthetic socket discussed in the Background section above. The system preferably includes one or more heat spreaders and a heat extraction subsystem. The heat spreader is preferably made of a sheet of high thermally conductive material, e.g., copper, aluminum, graphite, stainless steel, or similar type of metal material which meets the heat transfer requirements of a given patient that draws or absorbs heat from a large area of the residual limb on the prosthetic side and transports or dissipates the heat energy. The heat extraction subsystem draws or absorbs heat from the heat spreader and discharges or dissipates the heat to the environment side external to the socket.

The heat spreader preferably transfers heat from a relatively large area of the residual limb to the heat extraction subsystem through a relatively small cross-sectional area. The heat spreader may range in length depending on the diameter and length of the residual limb, e.g., the range of about 4" to about 10", although the heat spreader may be longer or shorter as needed. Typically, the heat spreader is between 1.5 and 4 inches wide and between 0.02 and 0.05 inches thick.

The heat extraction subsystem may vary in size depending on the particular needs of the patient, e.g., about 2" in length and width, although the subsystem may be larger or smaller as needed. One or more heat extraction subsystem devices may be used for a single heat spreader and a plurality of heat spreaders may be associated with a single heat extraction subsystem device. The one or more heat spreaders may be shaped as an elongated rectangle, oval, square, circle, or other shape based on the individual needs of the patient (disclosed below). One or more heat spreaders may be oriented such that they wrap around the limb circumferentially and/or run axially down the length of the limb (also disclosed below).

One or more heat spreaders may be attached to one or more components of a heat extraction subsystem using a thermal adhesive, a mechanical attachment, a combination thereof, or similar type of attachment technique. The mechanical attachment may include press-fitting the heat spreader into corresponding grooves in a heat extractor component, clamping between a pair of plates or between one plate and the body of a heat extractor component, or attaching it directly to the heat spreader using thermal tape or thermal pads, welding (e.g., by friction, deposition, resistance spot welding, and the like), brazing, direct attachment using pins, screws, or related hardware, snap fitting, or other known methods of mechanical attachment known to those skilled in the art.

Figure 2:
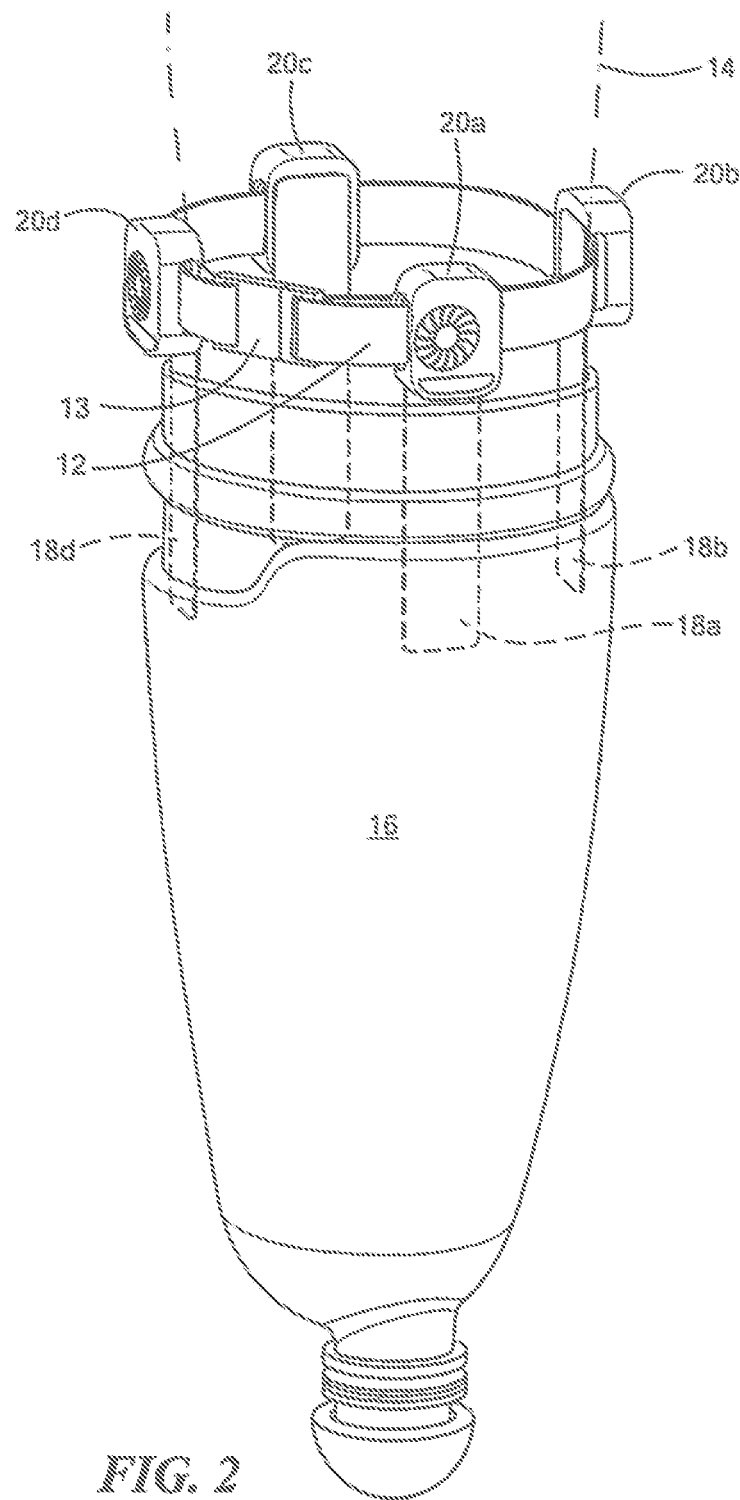
FIG. 2 is a schematic view showing the heat spreaders of the prosthetic socket cooling system of FIG. 1 in place underneath a prosthetic socket.

FIG. 1 shows an example of a prosthetic socket cooling system 10 including a strap 12 with buckle 13 for coupling about a limb 14, FIG. 2 fitted with prosthetic socket 16. Other methods of attaching the strap to the limb include hook and loop fasteners, snaps, hooks, or other means of mechanical attachment known to those skilled in the art. Extending from strap 12 (but not necessarily directly coupled thereto) are a plurality of spaced, lengthy, thin thermally conductive heat spreaders 18a, 18b, 18c, and 18d. A smaller number of larger, or a larger number of smaller width heat spreaders may be used. In one example, only one heat spreader located on the posterior of the leg is used. The one or more heat spreaders seat underneath prosthetic socket 16 (e.g., under a sock worn by the user, between the sock and the prosthetic socket liner, between the liner and the socket, between the liner and the limb, or the like). Rounded corners are preferred. In some examples, the heat spreaders are rectangular or elliptical in shape. In the design shown in phantom for heat spreader 18a, FIG. 1, the heat spreader may be T-shaped with concave head 19 conforming to the limb.

Figure 3:
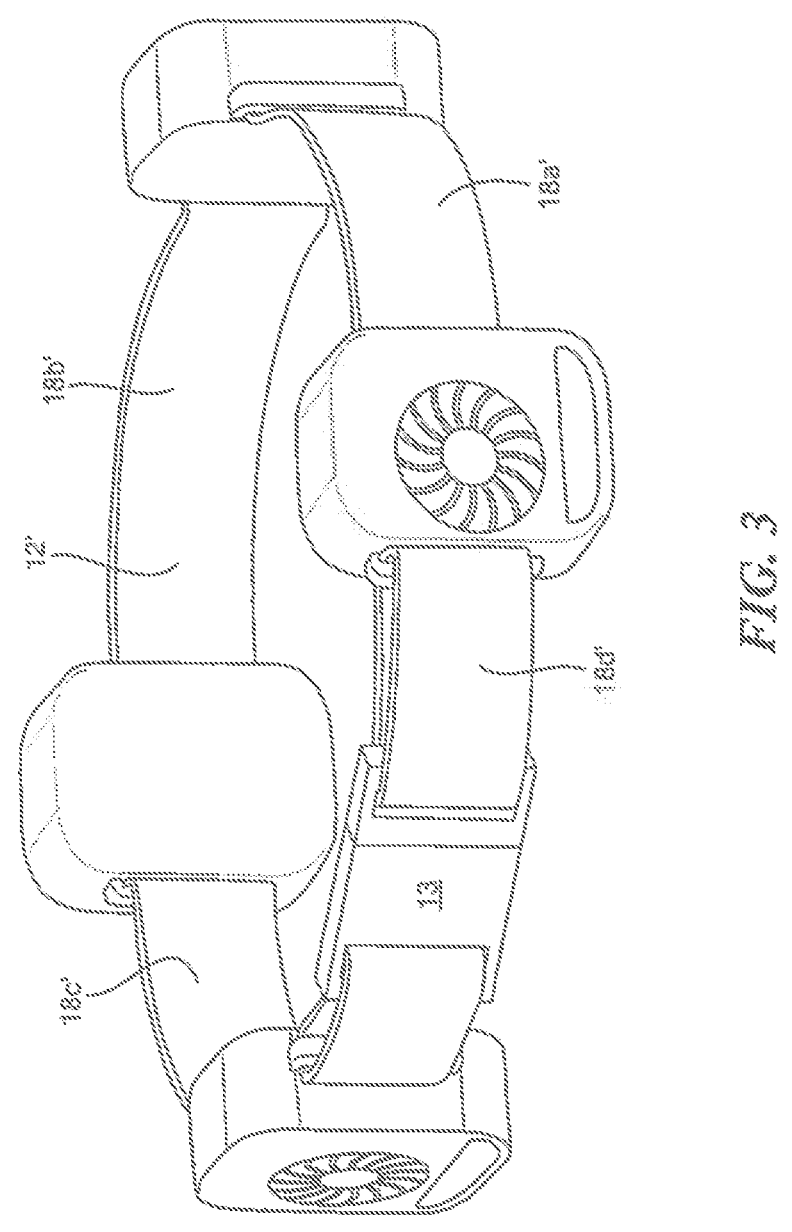
Figure 4:
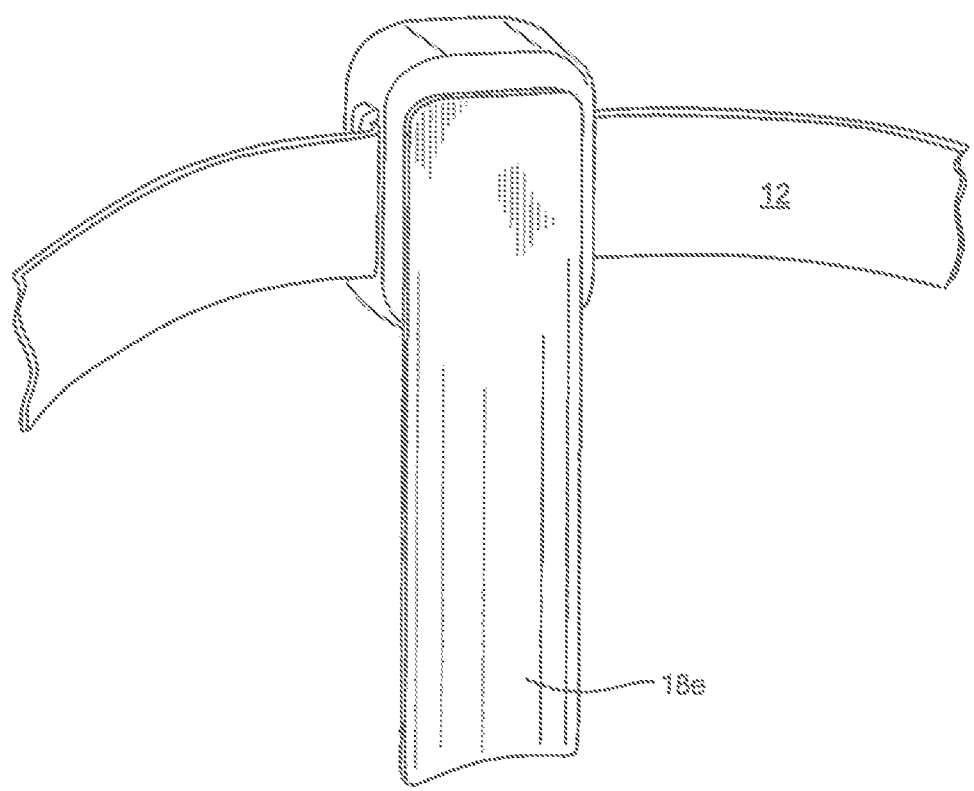
FIG. 4 is a schematic view showing a curved limb conforming heat spreader in accordance with aspects of the invention.

The strap 12 may also be made of or include thermally conductive material for cooling. Indeed, in the design of FIG. 3, the one or more heat spreaders 18a', 18b', 18c' and 18d' are sections of the strap. This strap may be worn with or without a prosthesis. The cooling band may be worn near the groin where the femoral artery is closest to the surface of the skin. The band may also be worn or on the arm. In the design of FIG. 4, a single large posteriorly located curved concave heat spreader 18e is used conforming to the limb.

There may be one or more heat extraction subsystems devices 20a, 20b, 20c, 20d, for each heat spreader although not every heat spreader may require its own device. The devices are typically disposed at the top of each heat spreader 18.

Figure 5:
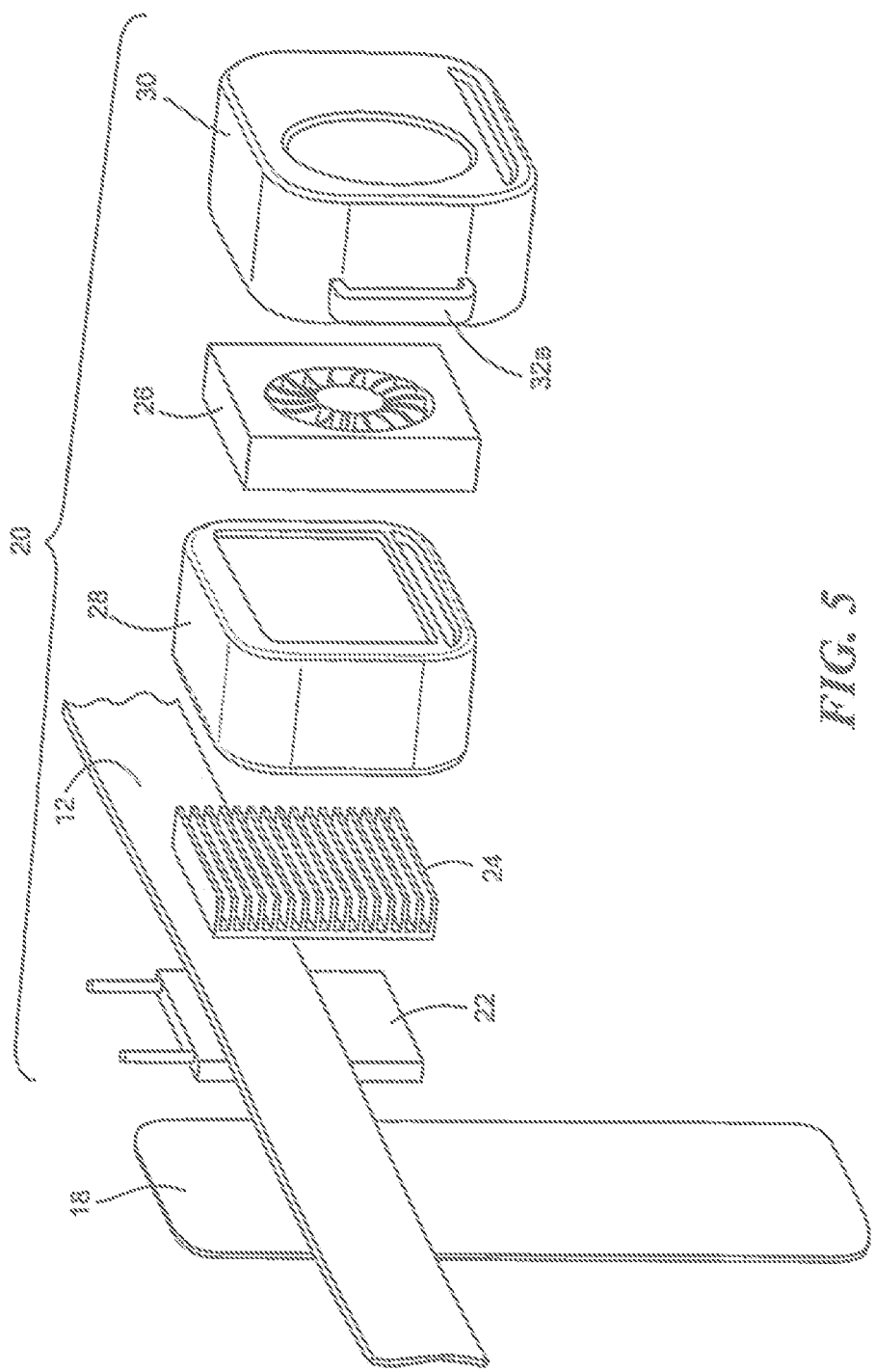
FIG. 5 is a schematic view showing the primary components associated with an example of a heat extraction subsystem for the prosthetic socket cooling system.

In FIG. 5, a heat extraction subsystem includes an optional Peltier-effect thermal electric cooler TEC 22 disposed between heat spreader 18 and finned heat sink 24 and fan 26. The fan 26 is configured to move air between the fins of heat sink 24 out to the environment or to blow air over the fins of heat sink 24. In other embodiments, the heat extraction subsystem device includes a TEC and a fan without a heat sink.

Strap 12 may be disposed between TEC 22 and heat sink 24 and made of a flexible, thermally-conductive material or provided with a cutout or thermally conductive area to allow effective heat transfer between TEC 22 and heat sink 24. One heat extraction subsystem device 20 includes housing sections 28 and 30 to form a housing for the device. Housing section 30 may include opposing slots 32a, 32b for strap 12. In some embodiments, TEC 22 is not used.

Figure 6:
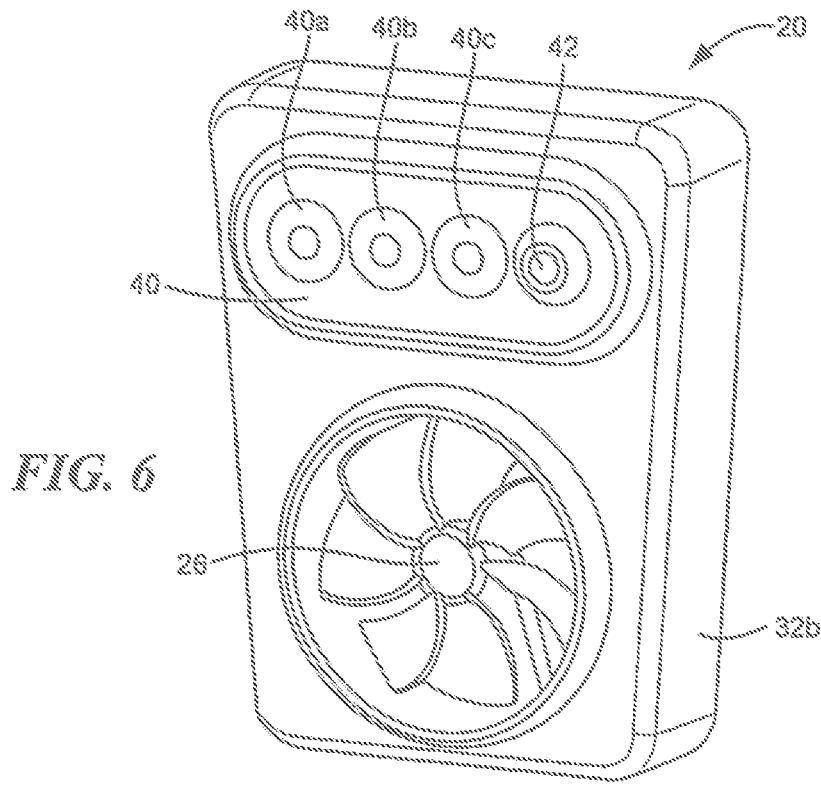
FIG. 6 is a schematic view an assembled heat extraction subsystem.
Figure 7:
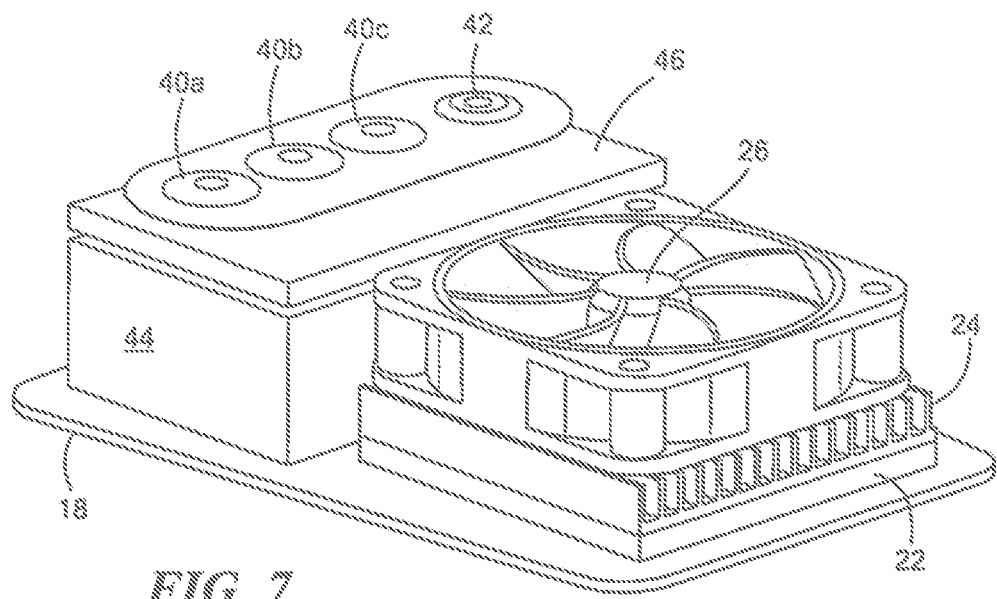
FIG. 7 is another schematic view of a heat extraction subsystem.
Figure 8:
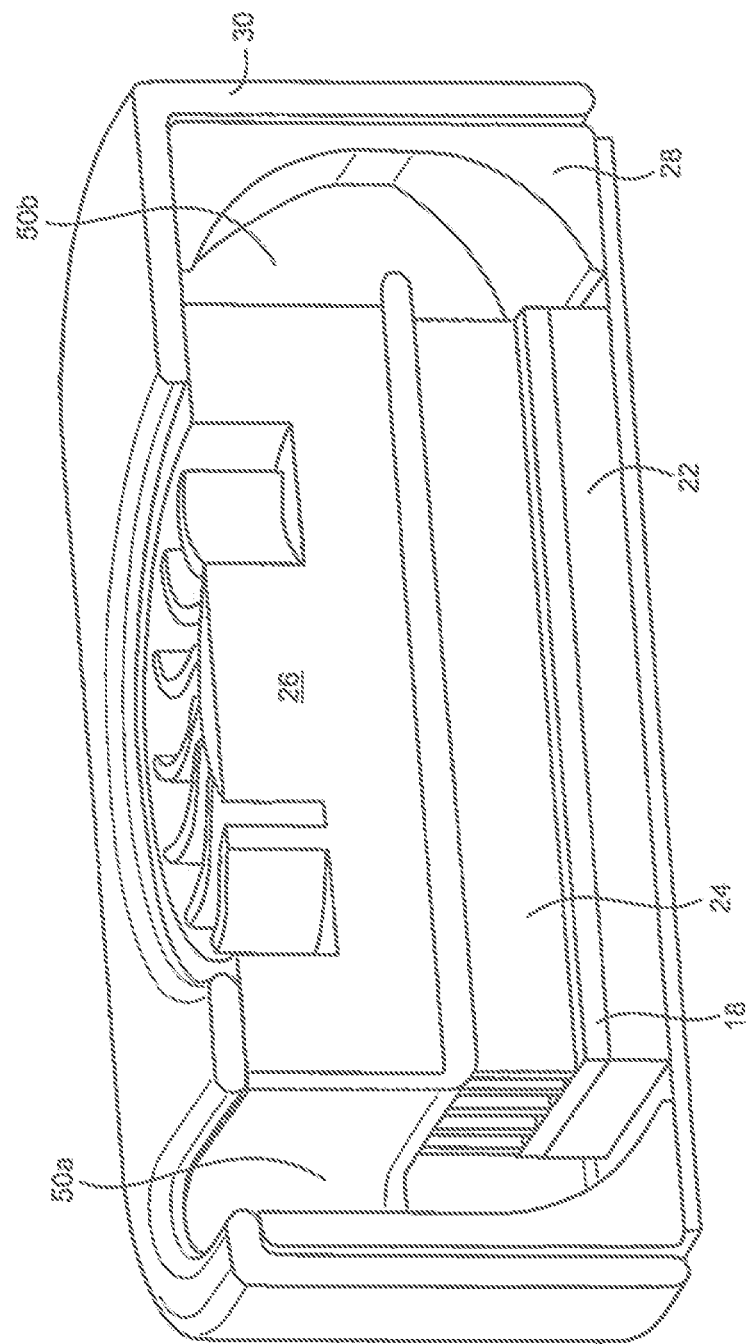
FIG. 8 is schematic cross sectional view showing the air channels formed by the housing sections of heat extraction subsystem.

In some embodiments, the heat extraction subsystem device includes user interface 40 with temperature control buttons 40a and 40b and on/off switch 40c, FIG. 6. Charging port 42 may be included for charging battery 44, FIG. 7. System 10 also preferably includes electronics section 46, e.g., a populated printed circuit board or similar type device. See also FIG. 8 where housing sections 28, 30 form air flow channels 50a and 50b.

Figure 9:
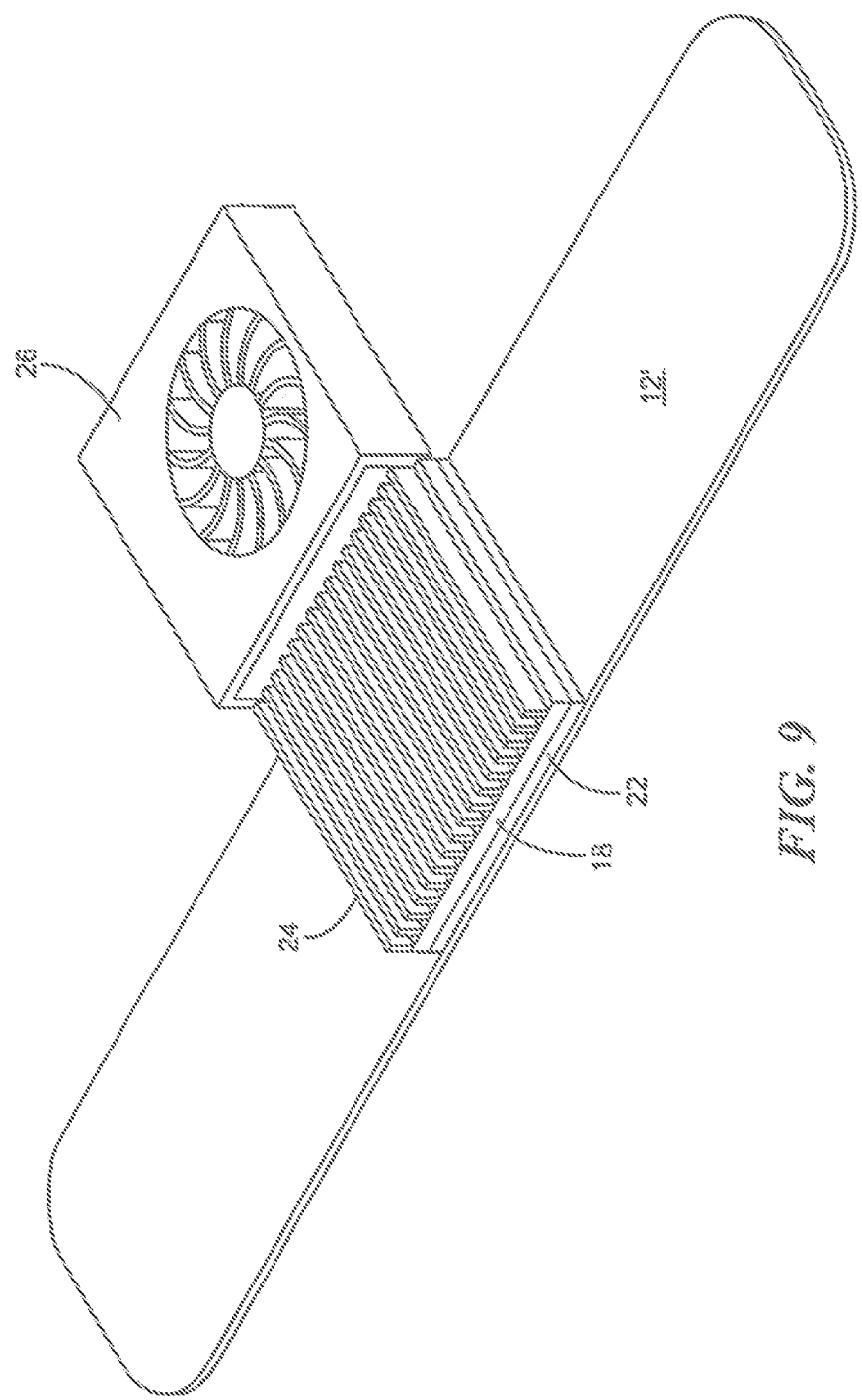
FIG. 9 is a schematic view showing an example of a heat extraction subsystem fan mounted adjacent a heat sink and TEC.

In FIG. 9, heat sink 24 is mounted to the heat spreader 12' and a centrifugal/blower fan 26 is located to the side of heat sink 24 and used to blow air over the fins thereof. This side-by-side configuration of the fan and heat sink could also be used in other configurations of the device such as that shown in FIG. 1. Heat spreader 12' may be a portion of the strap or connected to the strap.

Figure 10:
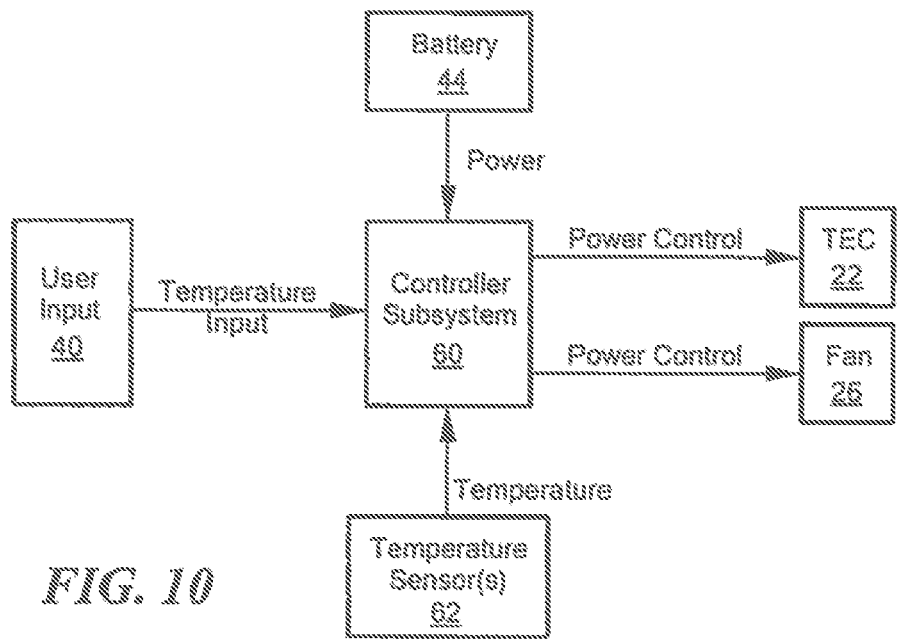
FIG. 10 is a block diagram showing one example of the primary components associated with a prosthetic socket cooling system.

As shown in FIG. 10, the electronic section may include controller subsystem 60 (e.g., one or more microprocessors, microcontrollers, field programmable gate arrays, or other logic devices or the like) may be configured (e.g., programmed) to operate fan 26 and/or the TEC 22 based on the outputs of user input 40 and, optionally, one or more temperature sensors 62.

Power may be applied to the TEC via the power adapter and the power source. The power source may be a battery, solar cell, or similar type power source as known by those skilled in the art. The power source applies a voltage across two dissimilar metals within the TEC to create a temperature difference via the Peltier effect which increases the rate of heat transfer from the heat spreader to the heat sink. The TEC transfers more heat to the fins which further increases the rate of heat exchange between the fins and the environment side. The TEC functions to reduce the temperature inside the socket. The power source coupled to the power adapter may be an external component linked with a wire or packaged together in the same housing. Control subsystem 60 preferably controls the power source to supply power to the TEC. A thermostat may be used to automatically adjust the power to the TEC to achieve an actively regulated temperature. The power source may be adjusted to control the power sent to the TEC and fan. The TEC and fan may be independently regulated with distinct current and voltages. The power source may be coupled to controls that allows the user to adjust the temperature set point of the thermal management device.

The user interface 40 may include a lower temperature button, an increase temperature button, an on/off button, and a charging connection as shown. The user interface allows the user to plug in the thermal management device to charge up a rechargeable battery (not shown), turn the thermal management device on or off, increase or lower the temperature to set temperature thresholds (discussed below), and provide control of the other various functions of the thermal management device. To increase the set point temperature, the user may press the increase temperature button. To decrease the set point temperature, the user may press the lower temperature button. In order to turn the device on an off, the user may press and hold the on/off button for three seconds for the power state change to occur. A battery, integrated with a heat extraction subsystem device or located externally, provides power to the electronic components.

Figure 11:
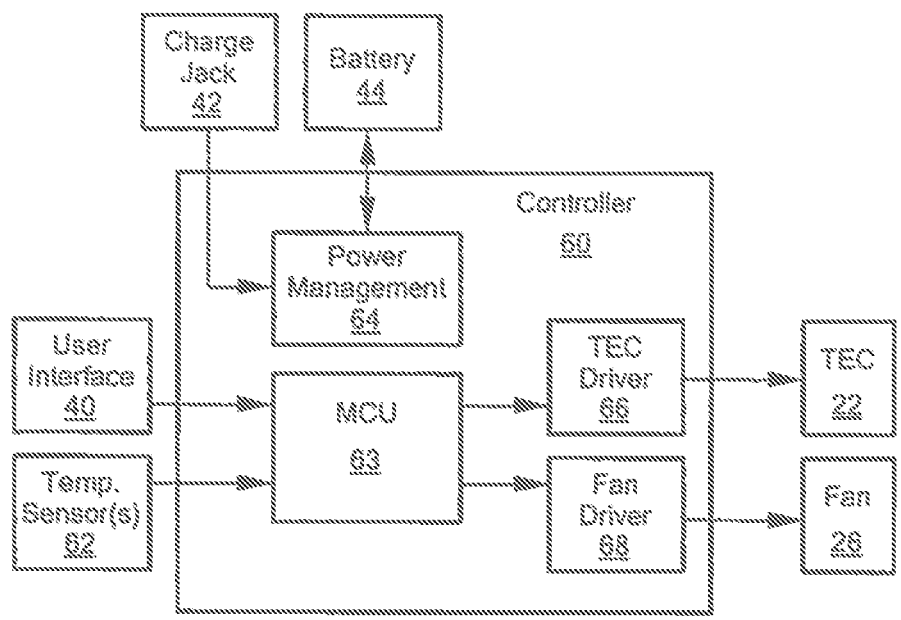
FIG. 11 is another block diagram showing additional details associated with an example of a prosthetic socket cooling system.

In one design, a printed circuit board (PCB) includes all the necessary electrical components known to those skilled in the art to manage the power of the heat extraction subsystem device, compute, and send/receive control signals to/from peripheral devices, e.g., the fan and the TEC shown. The PCB may include a controller subsystem, which includes a microprocessor unit (MCU) 63, FIG. 11, which may be programmed to manage the temperature within the prosthetic socket with input from temperature sensors as well as the temperature control input of the user interface. The PCB may also include a power management circuitry 64 which manages the input and charging of the battery as well as routing of power to the rest of the board. TEC and fan drivers, 66 and 68 control power to the TEC and fan.

Battery 44 may be a rechargeable lithium ion battery, or similar type battery. There are many different battery chemistries that may be suitable for the thermal management device for a prosthetic socket of one or more embodiments of this invention, e.g., lithium polymer, nickel-cadmium, and the like. The battery preferably powers all the various components. The battery may be charged via a charging connection on the device as discussed above or may be removable so it may be replaced with a fully charged battery. The charger for the device may be connected to an AC outlet and contains the necessary circuitry to correctly charge the device.

In some designs, temperature sensors 62, e.g., thermocouples, thermistors, or similar type device may be placed in preferred locations within prosthetic socket or the thermal management device to measure and evaluate the temperature of the residual limb of the user and the device to ensure safety and efficiency. The sensors may be placed to measure the temperature within the socket, the temperature of the cold-side of the TEC, the temperature of the hot-side of the TEC, and/or the ambient temperature of the environment outside of the heat extraction subsystem device.

In one example, current may be reversed to the TEC in order to provide heating for the prosthetic limb or temporarily slow the rate of cooling if the controller determines that cooling is occurring too rapidly.

The battery may provide power to the controller and peripheral components of the system discussed above. The user interface discussed above allows the user to raise or lower the desired temperature set point. The set point is then sent to the controller and is used to drive the control algorithms. The temperature sensors may capture the temperatures within the socket, on both sides of the TEC, as well as the ambient temperature, to determine the power needs of the TEC and fan.

The battery may provide power to the controller and peripheral components as discussed above. The user input allows the user to raise or lower the desired temperature set point. The set point is sent to the controller and is used to drive the control algorithms. The temperature sensors capture the temperatures within the socket and the ambient temperature to determine the power needs of the fan.

The battery may provide power to the controller and the peripheral components as discussed above. The user interface may include at least two buttons discussed above that allow the user to adjust the level or duration of desired cooling. Temperature sensors are preferably placed at strategic locations in the prosthetic socket or in the thermal management device to monitor temperature for safety as well as efficiency of the cooling system. Both of these inputs are provided as feedback to the MCU to determine optimal control signals for both the fan and TEC to accomplish the desired temperature. These control signals are then sent to the TEC and fan drivers to convert the control signals into the electrical power needed to drive the TEC and fan.

The battery may also provide power to the controller and the peripheral components, as discussed above. The user interface may include temperature control buttons as discussed above which allow the user to adjust the level of desired cooling. Temperature sensors may be placed at preferred locations in prosthetic socket or in the heat extraction subsystem to monitor temperature for safety as well as efficiency of the cooling system. Both of these inputs are provided as feedback to the microprocessor, and may be used in determining an optimal control signal for the fan to accomplish the desired temperature. This control signal is then sent to the fan driver to convert the control signal into the electrical power needed to drive the fan.

Figure 12:
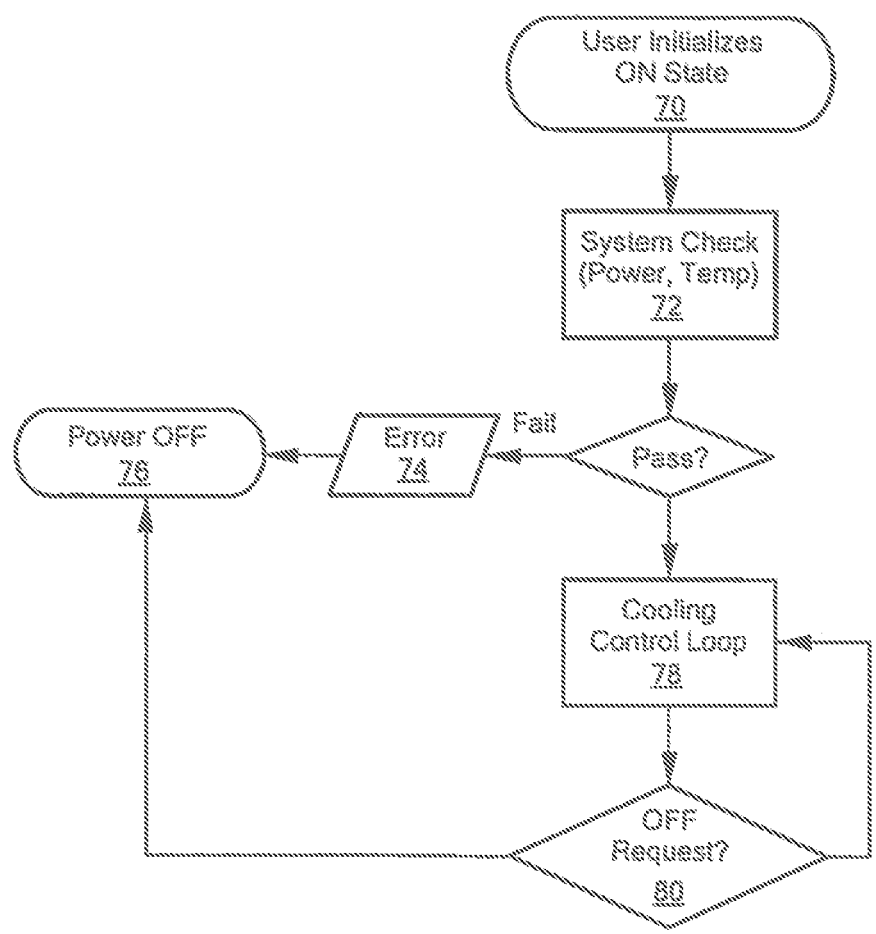
FIG. 12 is a flow chart showing an algorithm which may be executed by the controller of FIGS. 10 and 11.

One exemplary operation of the prosthetic socket cooling system and method thereof is now discussed with reference to FIGS. 12-14. In one example, the user turns the heat extraction subsystem device on using an ON/OFF button of the user interface step 70, FIG. 12. Once the 'ON' state is achieved, the device undergoes a system check, step 72. The system check establishes that all sensors, temperature readings, and input power are all within a pre-determined correct operating range. If any of these subsystems fail the check, the thermal management device will go into an error state, step 74 and power down as shown, step 76. If all the subsystems pass, step 72, the device check, the thermal management device then enters into the cooling control loop, step 78. At this point, the cooling control loop internally processes and executes all requests for temperature adjustments. The device will remain within the cooling control loop until an 'OFF' request is received, step 80. See, e.g., the Main Control Loop Pseudocode in the Exemplary Code below.

Figure 13A:
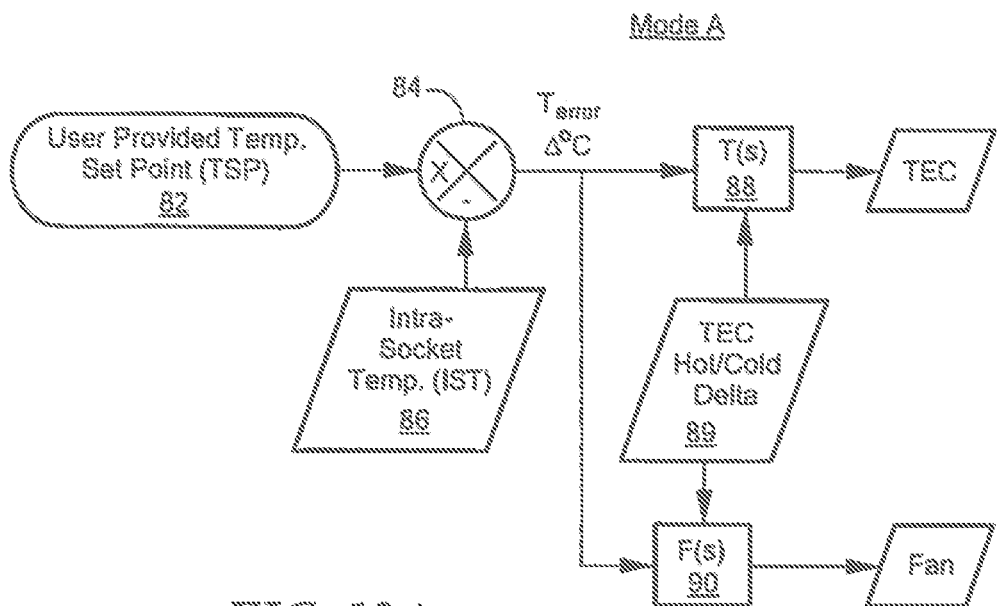
FIGS. 13A, 13B, 13C, 13D, 13E, and 13F are schematic views showing examples of a cooling control loop executed by the controller of FIGS. 10 and 11.

In one example, user provided temperature set point (TSP) 82, FIG. 13A, is preferably established based on input from a user. The TSP is then compared, step 84 to the intra-socket temperature (IST) using one or more temperature sensor(s) 62, step 86, to determine the difference, also known as the temperature error ($T_{error}$), between the actual temperature (IST) and the desired temperature (TSP). In one example, the IST may be weighted average of the output of multiple temperature sensors 62 at various locations inside the prosthetic socket, the hot-side of the TEC, the cold-side of the TEC, and/or on the skin of the residual limb, and/or any location in between cold-side of the TEC and the skin of the residual limb, using predetermined weighting factors. In another example, the IST may be the output of just one temperature sensor 62. The temperature error is then passed to the TEC transfer function, T(s), step 88. This transfer function preferably takes in the temperature error, and the temperature difference between the hot-side and cold-side of the TEC, indicated at 89. This function then computes the control signal that gives the TEC sufficient power to achieve the desired temperature while minimizing battery discharge rate. The control signal input $T_{error}$ may then be passed to another transfer function, F(s) 90, that computes a control signal that drives the fan at a certain RPM such that the TEC is able to perform at optimal performance for a given TSP, and TEC hot-side and cold-side temperatures. See, e.g., the Mode A Cooling Control Loop Pseudocode (TEC and FAN) in the Exemplary Code below, herein after "Mode A Cooling Control Loop".

Figure 13B:
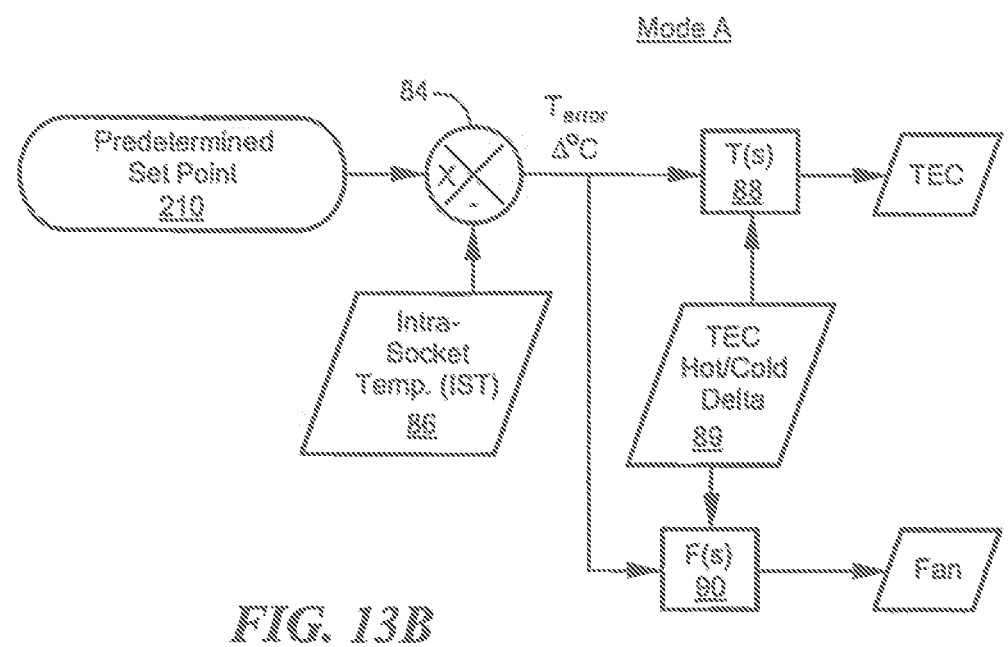

In another example, predetermined set point 210, FIG. 13B, may be provided using controller subsystem 60. Predetermined set point 210 may include a predetermined temperature set point, a predetermined heat flux set point of the TEC, a predetermined CoP set point, or a combination thereof. Predetermined set point 210 is then compared, step 84 to the intra-socket temperature (IST) using one or more temperature sensor(s) 62, step 86 to determine the difference, also known as the temperature error ($T_{error}$), between the actual temperature (IST) and predetermined set point 210. In one example, the IST may be weighted average of the output of multiple temperature sensors 62 at various locations inside the prosthetic socket, the hot-side of the TEC, the cold-side of the TEC, and/or on the skin of residual limb, and/or any location between cold-side of TEC and the skin of the residual limb using predetermined weighting factors. In another example, the IST may be the output of just one temperature sensor 62. The temperature error is then passed to the TEC transfer function, T(s), step 88. This transfer function preferably takes in the temperature error, the temperature difference between the hot and cold-side of the TEC, indicated at 89. This function then computes the control signal that gives the TEC sufficient power to achieve the desired temperature while minimizing battery discharge rate. The control signal input $T_{error}$ may then be passed to another transfer function, F(s) 90 that computes a control signal that drives the fan at a certain RPM such that the TEC is able to perform at optimal performance for a given TSP, ambient temperature, TEC hot-side and cold-side temperatures, and acceleration. See, e.g., the Mode A Cooling Control Loop for an example when predetermined set point 210 is a predetermined set point temperature. When predetermined set point 210 is a predetermined flux set point of the TEC, a predetermined CoP set point, or combination thereof, the Mode A Cooling Control Loop is appropriately modified as known by those skilled in the art.

Figure 13C:
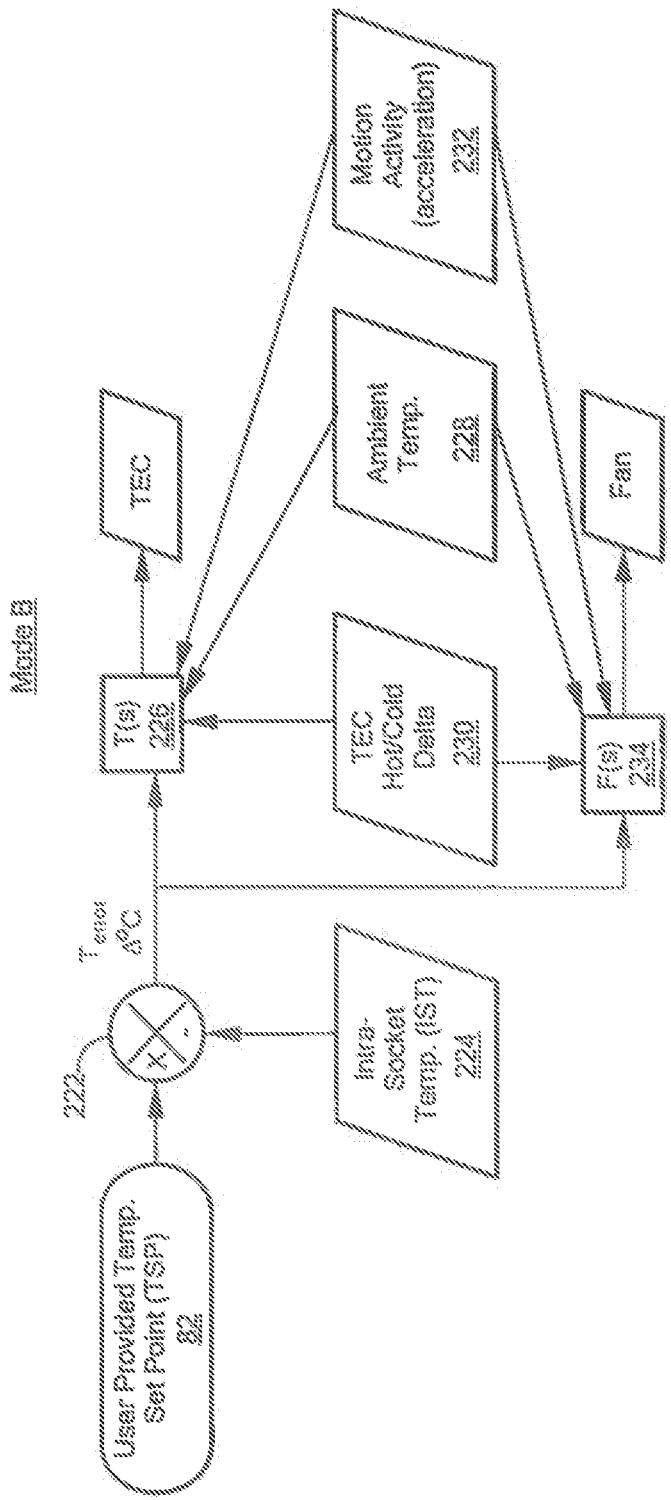

In another design, user provided TSP 82, FIG. 13C, is provided as discussed above. TSP 82 is then compared, step 222, to the intra-socket temperature (IST) using one or more temperature sensor(s) 62, step 224 to determine the difference, also known as the temperature error ($T_{error}$), between the actual temperature (IST) and TSP 82. In one example, the IST may be weighted average of the output of multiple temperature sensors 62 at various locations inside the prosthetic socket, the hot-side of the TEC, the cold-side of the TEC, and/or on the skin of residual limb, and/or any location between the cold-side of TEC and the skin of the residual limb, using predetermined weighting factors. In another example, the IST may be the output of just one temperature sensor 62. The temperature error is then passed to the TEC transfer function, T(s), step 226. This transfer function takes in the temperature error, the ambient temperature, indicated at 228, the temperature difference between the hot and cold-side of the TEC, indicated at 230, and motion activity or acceleration, indicated at 232. This function then computes the control signal that gives the TEC sufficient power to achieve the desired temperature while minimizing battery discharge rate. The control signal input $T_{error}$ may then be passed to another transfer function, F(s) 234, that computes a control signal that drives the fan at a certain RPM such that the TEC is able to perform at optimal performance for a given TSP, ambient temperature, TEC hot-side and cold-side temperatures, and acceleration. See, e.g., the Mode B Cooling Control Loop Pseudocode (TEC and FAN) in the Exemplary Code below, herein after "Mode B Cooling Control Loop".

Figure 13D:
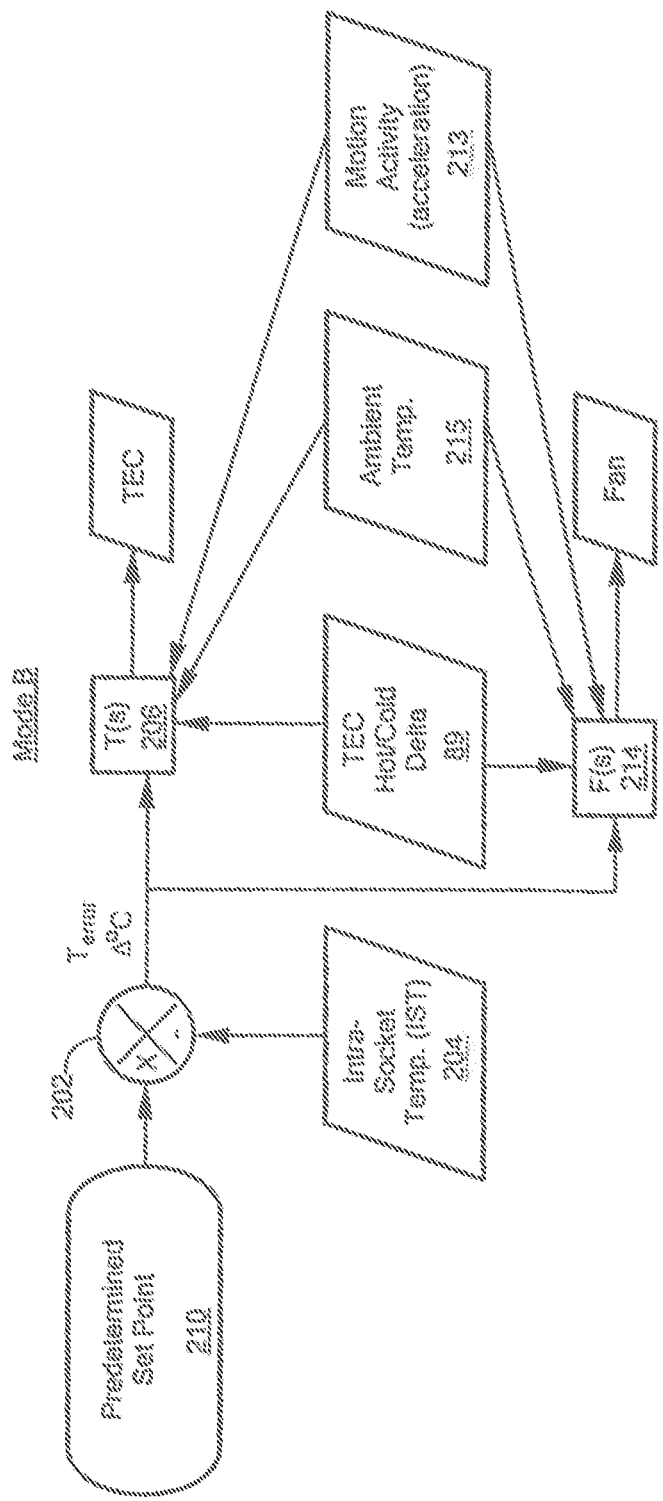

In another example, predetermined set point 210, FIG. 13D, may be provided using controller subsystem 60. Predetermined set point 210 may include a predetermined temperature set point, a predetermined heat flux set point of the TEC, a predetermined CoP set point, or a combination thereof. Predetermined set point 210 is then compared, step 202 to the intra-socket temperature (IST) using one or more temperature sensor(s) 62, step 204 to determine the difference, also known as the temperature error ($T_{error}$), between the actual temperature (IST) and predetermined set point 210. In one example, the IST may be weighted average of the output of multiple temperature sensors 62 at various locations inside the prosthetic socket, the hot-side of the TEC, the cold-side of the TEC, and/or on the skin of residual limb, and/or any location between the cold-side of TEC and the skin of the residual limb using predetermined weighting factors. In another example, the IST may be the output of just one temperature sensor 62. The temperature error is then passed to the TEC transfer function, T(s), step 206. This transfer function takes in the temperature error, ambient temperature 215, the temperature difference between the hot-side and cold-side of the TEC, indicated at 211, and motion activity or acceleration 213. This function then computes the control signal that gives the TEC sufficient power to achieve the desired temperature while minimizing battery discharge rate. The control signal input $T_{error}$ may then be passed to another transfer function, F(s) 214 that computes a control signal that drives the fan at a certain RPM such that the TEC is able to perform at optimal performance for a given TSP, ambient temperature, TEC hot-side and cold-side temperatures, and acceleration. See, e.g., the Mode B Cooling Control Loop Pseudocode (TEC and FAN) in the Exemplary Code below for an example when predetermined set point 210 is a predetermined set point temperature. When predetermined set point 210 is a predetermined flux set point of the TEC, a predetermined CoP set point, or combination thereof, the Mode B Cooling Control Loop is appropriately modified as known by those skilled in the art.

Figure 13E:
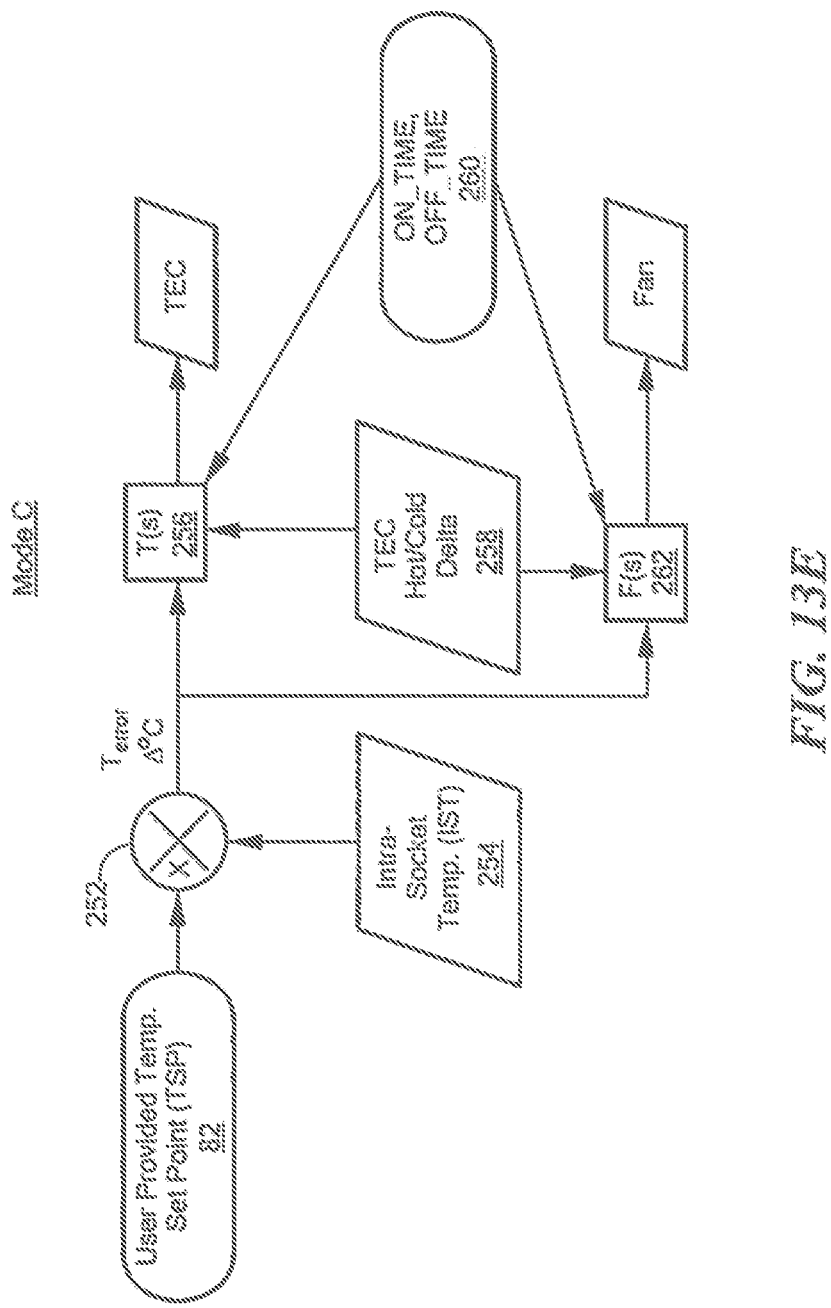

In yet another design, TSP 82, FIG. 13E, is provided as discussed above. The TSP is then compared, step 252 to the intra-socket temperature (IST) using one or more temperature sensor(s) 62, step 254, to determine the difference, also known as the temperature error ($T_{error}$), between the actual temperature (IST) and the desired temperature TSP 82. In one example, the IST may be weighted average of the output of multiple temperature sensors 62 at various locations inside the prosthetic socket, the hot-side of the TEC, the cold-side of the TEC, and/or on the skin of the residual limb, and/or any location in between cold-side of TEC on the skin of the residual limb, using predetermined weighting factors. In another example, the IST may be the output of just one temperature sensor 62. The temperature error is then passed to the TEC transfer function, T(s), step 256. This transfer function takes in the temperature error, the temperature difference between the hot and cold-side of the TEC, indicated at 258, and the ON TIME/OFF TIME, indicated at 260. This function then computes the control signal that gives the TEC sufficient power to achieve the desired temperature while minimizing battery discharge rate. The control signal input $T_{error}$ and ON TIME/OFF TIME 260 may then be passed to another transfer function, F(s) 262, that computes a control signal that drives the fan at a certain RPM such that the TEC is able to perform at optimal performance for a given TSP, ambient temperature, TEC hot-side and cold-side temperatures, and ON TIME/OFF TIME 260. See, e.g., the Mode C Cooling Control Loop Pseudocode (TEC and FAN) in the Exemplary Code below, herein after "Mode C Cooling Control Loop".

Figure 13F:
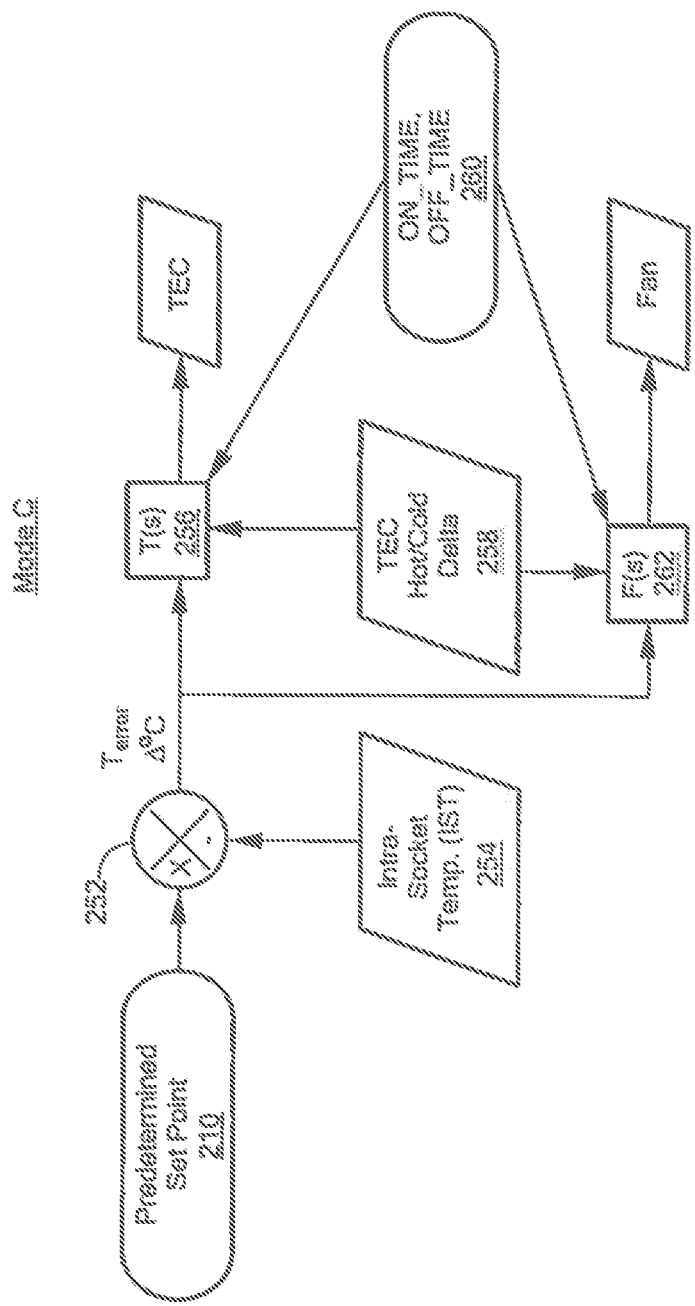

In another example, predetermined set point 210, FIG. 13F, may be provided using controller subsystem 60. Predetermined set point 210 may include a predetermined temperature set point, a predetermined heat flux set point of the TEC, a predetermined CoP set point, or a combination thereof. Predetermined set point 210 is then compared, step 252 to the intra-socket temperature (IST) using one or more temperature sensor(s) 62, step 254 to determine the difference, also known as the temperature error ($T_{error}$), between the actual temperature (IST) and predetermined set point 210. In one example, the IST may be weighted average of the output of multiple temperature sensors 62 at various locations inside the prosthetic socket, the hot-side of the TEC, the cold-side of the TEC, and/or on the skin of residual limb, and/or any location between the cold-side of TEC and the skin of the residual limb using predetermined weighting factors. In another example, the IST may be the output of just one temperature sensor 62. The temperature error is then passed to the TEC transfer function, T(s), step 256. This transfer function takes in the temperature error, the temperature difference between the hot-side and the cold-side of the TEC, indicated at 258, and the ON TIME/OFF TIME, indicated at 260. This function then computes the control signal that gives the TEC sufficient power to achieve the desired temperature while minimizing battery discharge rate. The control signal input $T_{error}$ and ON TIME/OFF TIME 260 may then be passed to another transfer function, F(s) 262, that computes a control signal that drives the fan at a certain RPM such that the TEC is able to perform at optimal performance for a given TSP, ambient temperature, TEC hot-side and cold-side temperatures, and ON TIME/OFF TIME 260. See, e.g., the Mode C Cooling Control Loop Pseudocode (TEC and FAN) in the Exemplary Code below for example when predetermined set point 210 is a predetermined set point temperature. When predetermined set point 210 is predetermined flux set point of the TEC, a predetermined CoP set point, or a combination thereof, the Mode C Cooling Control Loop is appropriately modified as known by those skilled in the art.

Figure 14:
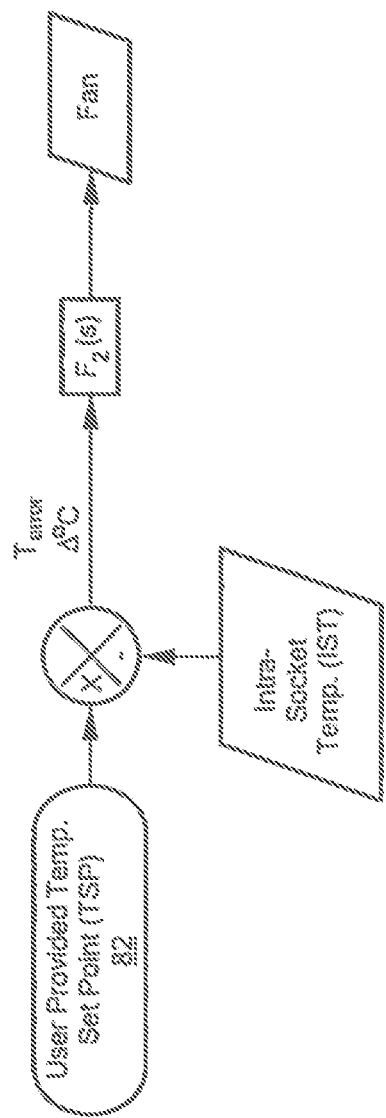
FIG. 14 is a flow chart showing another example of a cooling control loop algorithm executed by the controller shown in one or more of FIGS. 10-13E.

If the TEC is not used, the temperature set point TSP 82, FIG. 14, may be established based on input from the user, e.g., using lower temperature or increase temperature button. The TSP is then compared to the Intra-Socket temperature (IST) to determine the difference, also known as the temperature error ($T_{error}$), between the actual temperature (IST) and the desired temperature (TSP). The temperature error is then passed to the fan transfer function, $F_2(s)$. This transfer function takes in the temperature error (and other variables) and computes a control signal that drives the fan at a certain RPM such that the desired temperature is achieved. See, e.g., The Cooling Control Loop Pseudocode (Fan only) in the Exemplary Code below.

Figure 15:
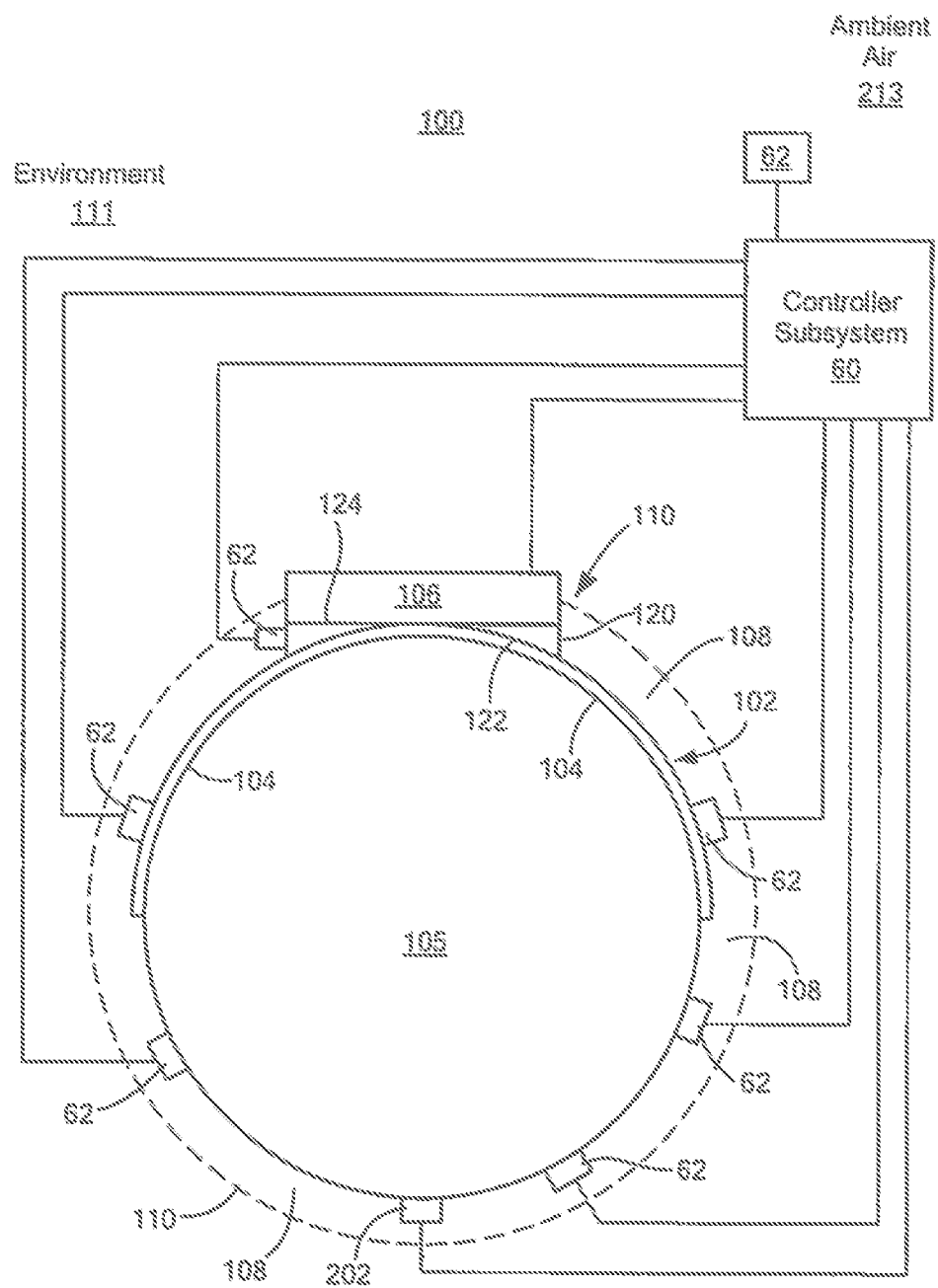
FIG. 15 is a schematic view showing another example of a prosthetic socket cooling system.
Figure 16A:
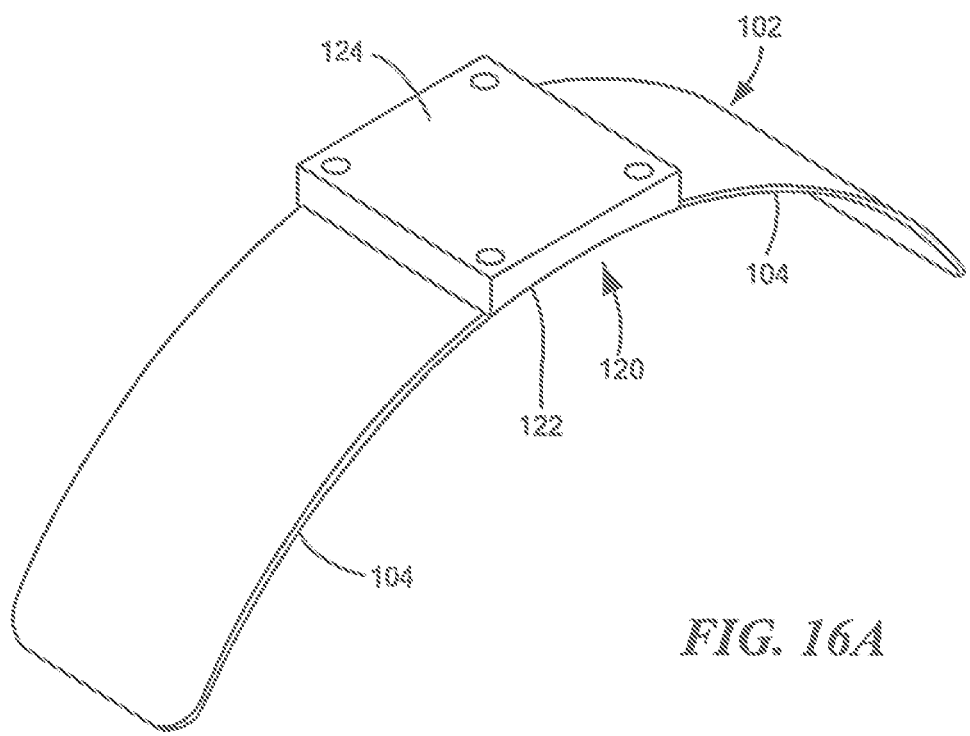
FIGS. 16A and 16B are schematic three-dimensional views showing in further detail one example of the thermally conductive adapter plate shown in FIG. 15.
Figure 16B:
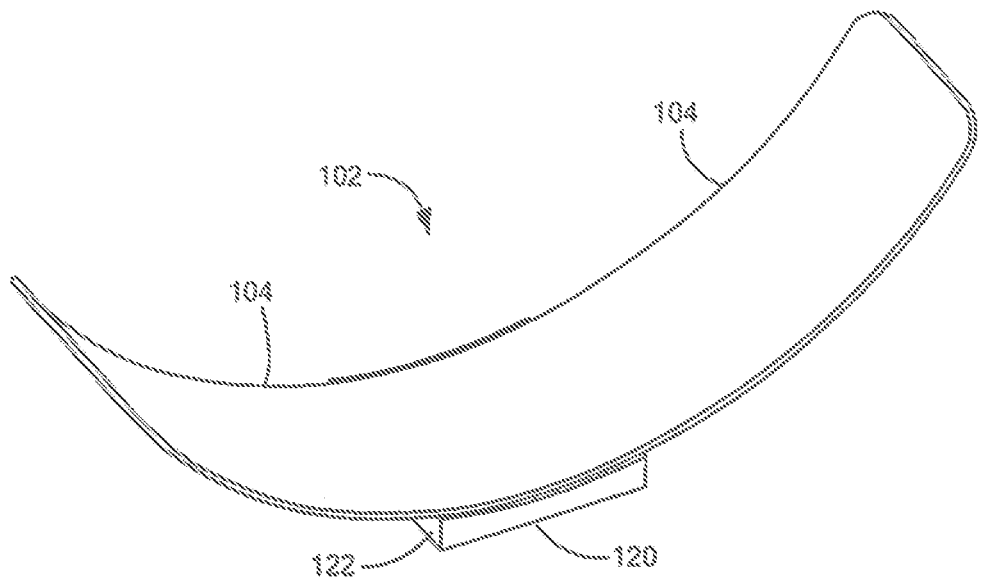

Prosthetic cooling system 100, FIG. 15, of another embodiment of this intervention, preferably includes thermally conductive heat spreader 102 which is preferably curved to contour to residual limb 105 as shown to provide for curved shaped portion 104 which is configured to maximize contact with residual limb 105 of a user as shown. In operation, heat spreader 102 is typically manufactured initially flat and straight and is curved by a user to conform to the shape of residual limb 105. In one design, thermally conductive heat spreader 102 with curved shaped portion 104 is preferably made of a high thermally conductive material, e.g., copper, aluminum, graphite, stainless steel, or similar type thermally conductive material which absorbs heat from the area of contact of thermally conductive heat spreader 102 with residual limb 105. FIGS. 16A and 16B shows in further detail one example of curved shaped portion 104 of thermally conductive heat spreader 102 comprised of a high thermally conductive material. In one design, thermally conductive heat spreader 102, FIGS. 15-16B, preferably has a length of about 9 inches, a width of about 3 inches and a thickness in the range of about 0.01 inches to about 0.05 inches. In other designs, the length may be longer or shorter and the thickness may be thinner or thicker. Thermally conductive heat spreader 102 spreader preferably transfers heat from the area of contact with residual limb 105, FIG. 15, to heat extraction subsystem 106, as discussed below.

Figure 17:
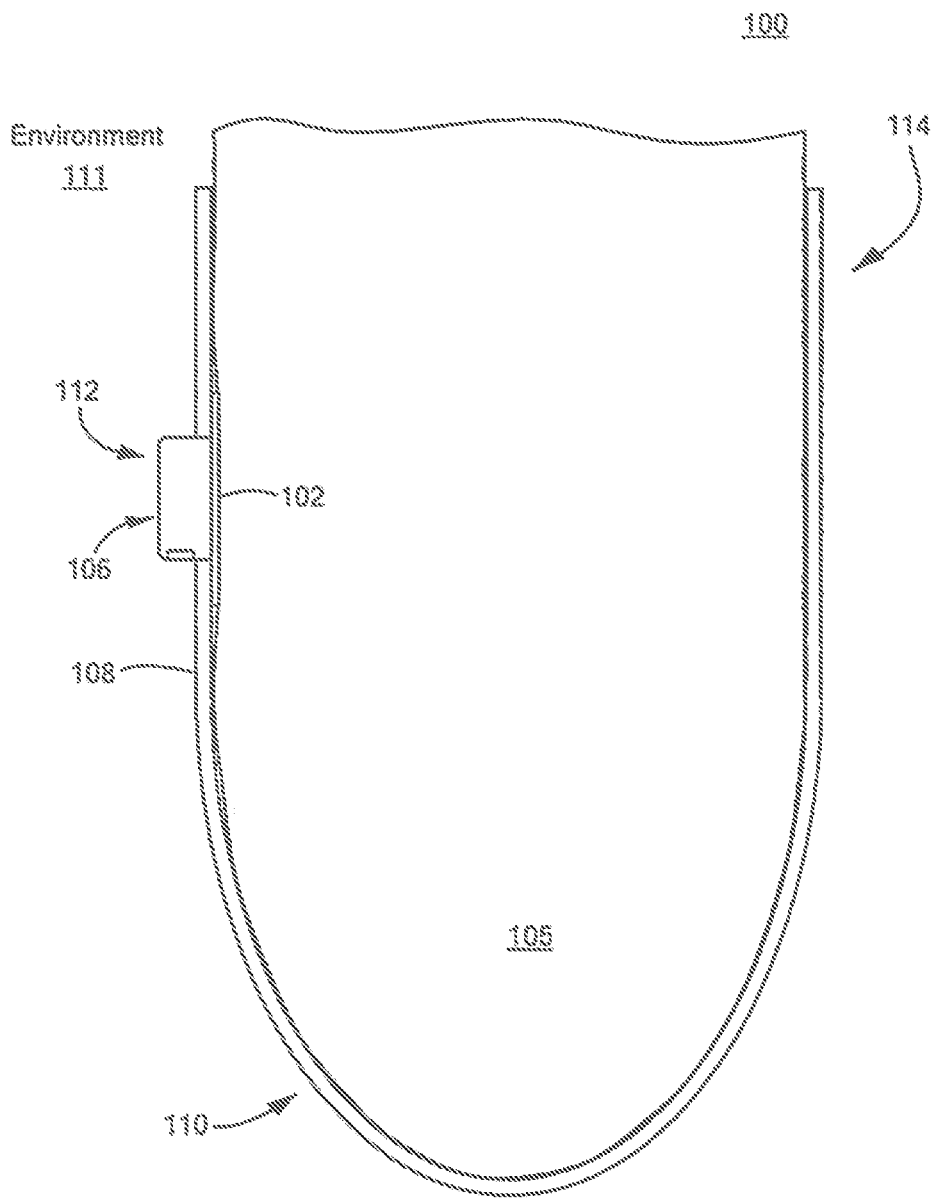
FIG. 17 is a schematic end-view showing in further detail one example of the heat extraction subsystem shown in FIG. 15 coupled through the wall of a prosthetic socket and to the thermally conductive heat spreader.
Figure 18B:
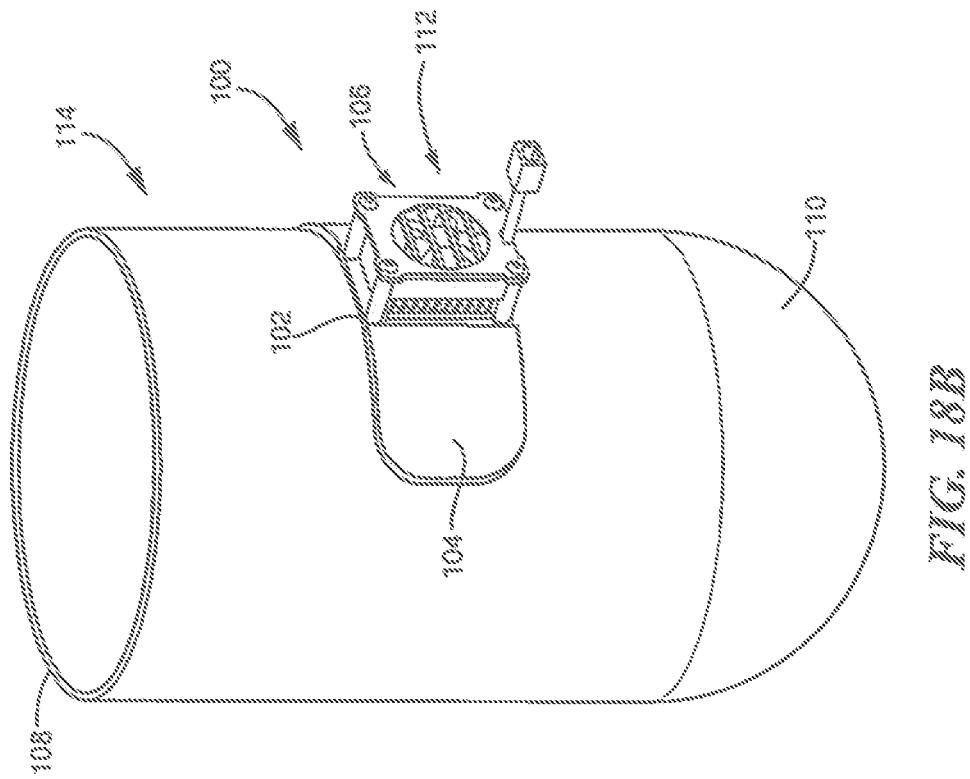
FIGS. 18A and 18B are three-dimensional views showing in further detail another example of the heat extraction subsystem shown in FIG. 15 coupled through the wall of a prosthetic socket and to the thermally conductive heat spreader.
Figure 18A:
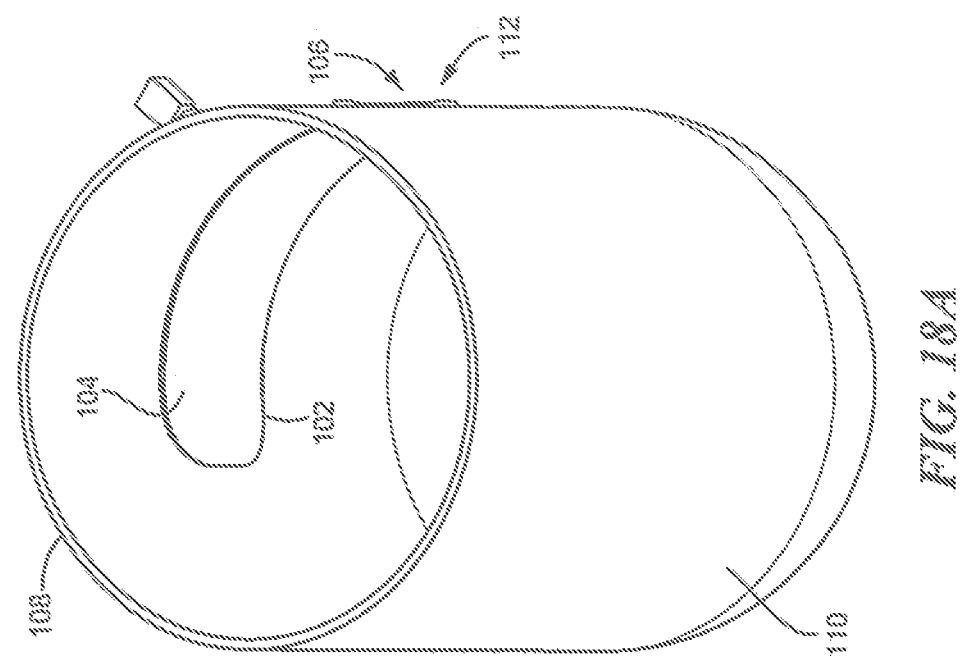

System 100, FIG. 15, also includes heat extraction subsystem 106 coupled through wall 108 of prosthetic socket 110 and coupled to thermally conductive heat spreader 102 as shown. FIG. 17 shows in further detail one example of heat extraction subsystem 106 coupled through wall 108 of prosthetic socket 110 and to thermally conductive heat spreader 102 with curved shaped portion 104, FIGS. 15-16B, configured to maximize contact with residual limb 105 of the user. FIGS. 18A and 18B shows in further detail one example of the heat extraction subsystem 106 coupled through wall 108 of prosthetic socket 110 and to the thermally conductive heat spreader 102 with curved portion 104.

In one design, thermally conductive heat spreader 102 and heat extraction subsystem 106 are preferably positioned at a location near mid-location 112, FIGS. 17, 18A, and 18B, of prosthetic socket 110 as shown. In other examples, thermally conductive heat spreader 102 and heat extraction subsystem 106 may be located near upper-location 114.

Heat extraction subsystem 106 draws or absorbs heat from the thermally conductive heat spreader 102 and discharges or dissipates the heat to environment 111 external to prosthetic socket 110.

Figure 19A:
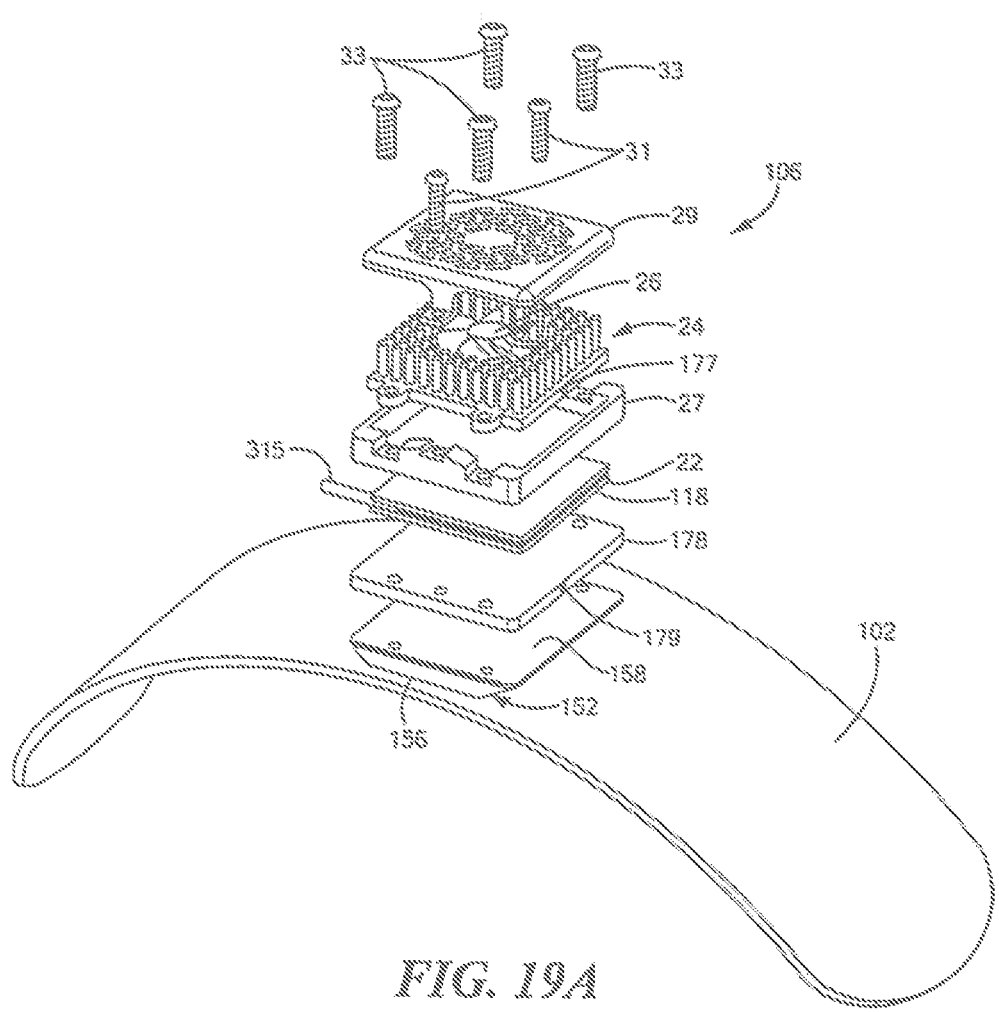
Figure 19B:
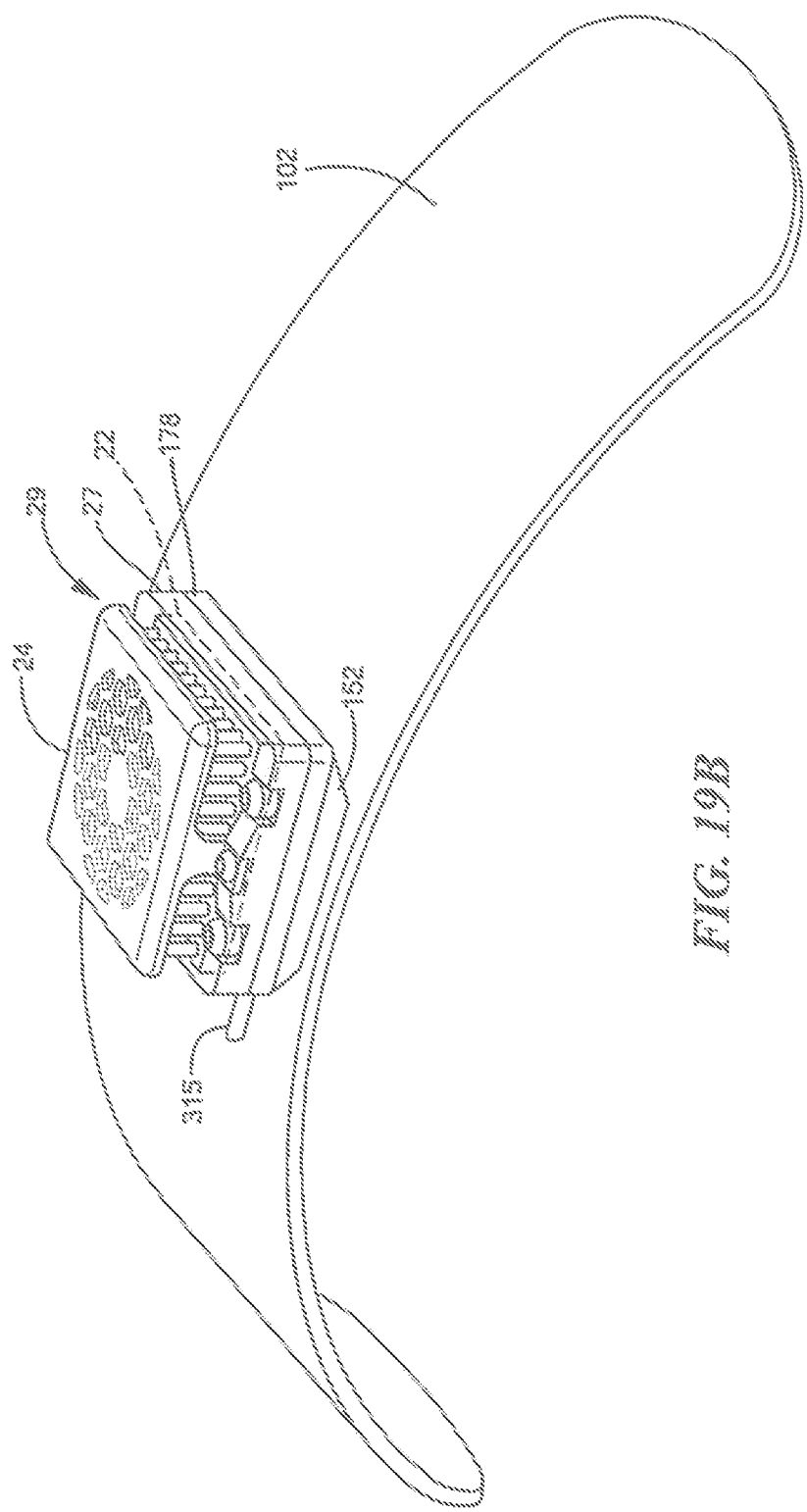

In one design, heat extraction subsystem 106 preferably includes thermoelectric cooler (TEC) 22, FIGS. 19A and 19B, e.g., a Peltier-Effect TEC, or similar type device similar as discussed above with reference to one or more of FIGS. 1-18B. Preferably, TEC 22. FIGS. 19A and 19B, has a predetermined shape, e.g., a square or rectangular shape as shown, and includes flat surface 118, FIG. 19A, preferably having a predetermined surface area. In one example, the surface area of TEC 22 is about 40 mm by about 40 about mm. In other examples, the surface area of TEC 22 may be larger or smaller surface than 40 mm by 40 about mm. In one design, TEC 22 may have a thickness of about 3.2 mm. In other designs, TEC 22 may have thickness greater or less than 3.2 mm. Heat extraction subsystem 106 also preferably includes heat sink 24 and fan 26 as shown. In one design, heat sink 24 may include opening 177 configured to receive a temperature sensor, thermistor, or similar type device configured to measure temperature of the hot-side of TEC 22. Fan 26 is preferably configured to move air between the fins of heat sink 24 and out into environment 111, FIGS. 15 and 17, from prosthetic socket 110 or blow air over the fins of heat sink 24, e.g., as discussed above with reference to one or more of FIGS. 1-18B. Heat extraction subsystem 106, FIG. 19A, may also include TEC cover 27 and fan protective cover 29. In one design, heat extraction subsystem 106 preferably includes thermally conductive adapter 152 (discussed below) and thermally conductive spacer 178 preferably coupled between TEC 22 and thermally conductive adapter 152. In one design, thermally conducive spacer 178 may include opening 179 configured to receive a temperature sensor, thermistor, or similar type device configured to measure the temperature of at least the cold-side of TEC 22. One or more fasteners, e.g., screws 33, couple all the components of heat extraction 106 discussed above together as shown in FIGS. 19B and 19C. In one design, the one or more fasteners may be made of a non-thermally conductive or insulating material, e.g., nylon, plastic or similar type material. Heat extraction subsystem 106 also preferably includes connection device 313, FIG. 19C, which connects TEC 22 via line 315 (also shown in FIGS. 19A and 19B) to controller subsystem 60, FIG. 15.

Thermally conductive heat spreader 102, FIGS. 15-19B, having curved shaped portion 104 provides maximum contact with residual limb 105 such that prosthetic cooling system 100 effectively and efficiently extracts heat from residual limb 105. Heat extraction subsystem 106 preferably absorbs the heat from thermally conductive heat spreader 102 and expels warm air into environment 111 from prosthetic socket 110 such that system 100 maintains a desired temperature inside prosthetic socket 110, e.g., a temperature in the range of about 50° F. to about 95° F., as discussed in detail below. The coefficient of performance (CoP) of system 100 is preferably improved by thermally conductive heat spreader 102 because of the large amount of surface area engaged by thermally conductive heat spreader 102 with residual limb 105. This provides for efficient heat flow from residual limb 105 to heat extraction subsystem 106 at a lower temperature gradient. Thus, the various components of heat extraction subsystem 106, e.g., TEC 22, may not need to be as cold and therefore may use less power. A reduction in power consumption allows the use of lower voltages by TEC 22. Thermally conductive heat spreader 102 is preferably optimally sized to effectively extract heat from residual limb 105, e.g., the point at which an increase in size of thermally conductive heat spreader 102 no longer results in an increase in CoP is associated with the geometrical, thermal, and electrical characteristics of heat spreader 102.

Figure 20A:
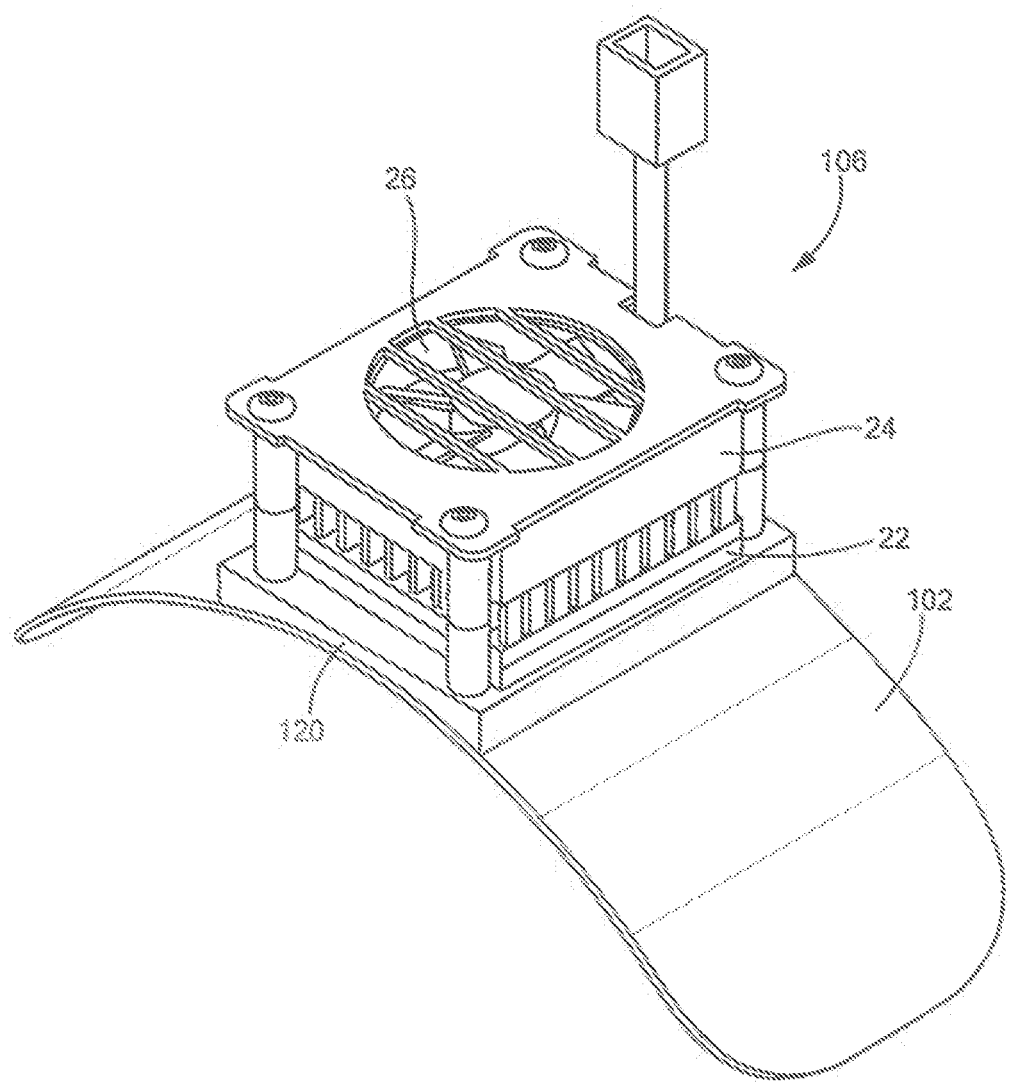
FIGS. 20A and 20B are schematic three-dimensional views showing in further detail one example the primary components of the heat extraction subsystem shown in one or more of FIGS. 15-18B.
Figure 20B:
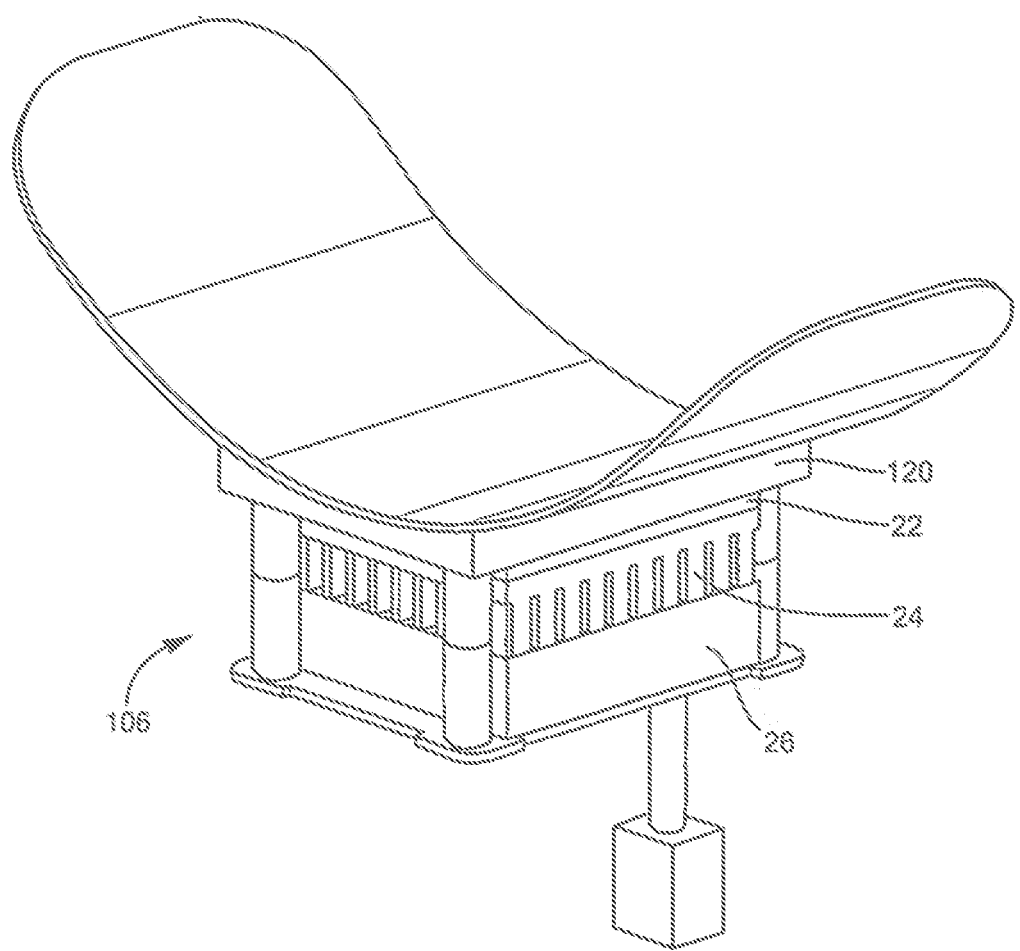

In one design, prosthetic cooling system 100, FIG. 15, preferably includes thermally conductive adapter 120 coupled between thermally conductive heat spreader 102 and heat extraction subsystem 106 as shown. Thermally conductive adapter 120 preferably includes curved surface 122 on one side configured to approximately match curved shaped portion 104 of thermally conductive heat spreader 102 and flat surface 124 on the other side configured to approximately match flat surface 118, FIG. 19A, of TEC 22. Thermally conductive adapter 120, FIG. 15, is also preferably configured to approximately match the shape, e.g., a square or a rectangular shape of TEC 22 and the surface area of TEC 22 discussed above. FIGS. 16A-16B show in further detail one example of the structure of thermally conductive adapter 120 with curved portion 104 coupled to thermally conductive heat spreader 102 with curved surface 122 and flat surface 124 as shown. FIGS. 20A and 20B show one example of heat extraction subsystem 106 coupled to thermally conductive adapter 120 coupled to thermally conductive heat spreader 102.

Figure 23A:
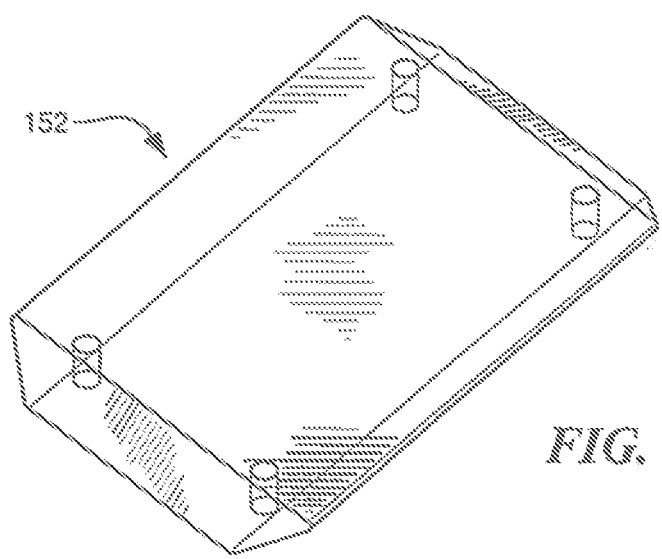
FIG. 23A is a schematic three-dimensional top-side view of the thermally conductive adapter shown in FIGS. 21 and 22.
Figure 23B:
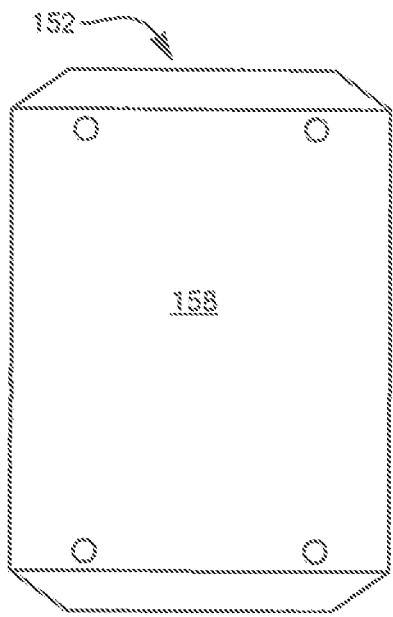
FIG. 23B is a schematic three-dimensional top-view of the thermally conductive adapter shown in FIGS. 21 and 22.
Figure 23C:
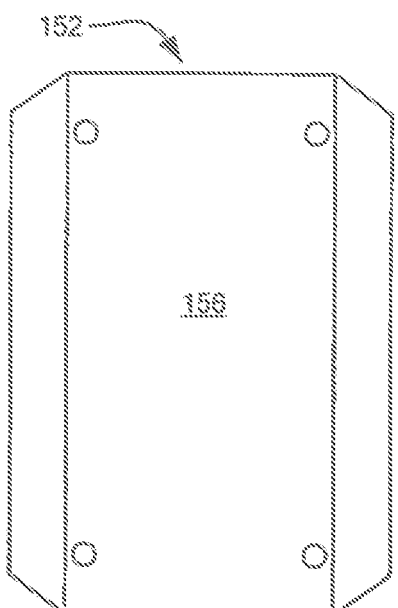
FIG. 23C is a schematic three-dimensional bottom-view of the thermally conductive adapter shown in FIGS. 21 and 22.

In another design, system 100 may include thermally conductive heat spreader 102, FIGS. 21 and 22, which includes flat portion 150. In this example, system 100 also preferably includes thermally conductive adapter 152 (also shown in FIG. 19A) which includes flat surface 156 on one side configured to approximately match flat portion 150 of thermally conductive heat spreader 102 and flat surface 158 on the other side configured to approximately match the flat surface 118 of TEC 22 and the predetermined shape and surface area of TEC 22. System 100 may also include thermally conductive spacer 178 (also shown in FIG. 19A) coupled between TEC 22 and thermally conductive adapter 152 as shown. In other designs, thermally conductive spacer 178 may not be utilized. As discussed above, thermally conductive heat spreader 102 also includes curved shaped portion 104 which conforms to residual limb 105. FIG. 22 shows in further detail one example of thermally conductive adapter 152 including flat surface 158 of thermally conductive adapter 152 which approximately matches flat surface 118, FIG. 19A, and the predetermined shape and surface area of TEC 22. FIG. 23A shows a three-dimensional top-side view showing in further detail one example of the structure of thermally conductive adapter 152. FIG. 23B shows in further detail top side 158 of thermally conductive adapter 152 which may be coupled to thermally conductive spacer 178 or directly to TEC 22. FIG. 23C shows in further detail flat surface 156 of thermally conductive adapter 152, which is coupled to flat portion 150 of thermally conductive heat spreader 102. Flat surface 156 preferably has a narrow width as shown such that thermally conductive heat spreader 104 may efficiently conform to the shape of residual limb 105 and efficiently extract heat therefrom.

Thermally conductive adapter 120 preferably conforms to the shape of residual limb 105, FIG. 15, to provide a universal fit by reducing the flat surface area exposed to the cylindrical shaped residual limb 105 such that system 100 effectively and efficiently transfers heat from thermally conductive heat spreader 102 to heat extraction subsystem 106 and maintains a desired temperature inside prosthetic socket 110, e.g., in the range of about 50° F. to about 95° F., as discussed in detail below.

Figure 24:
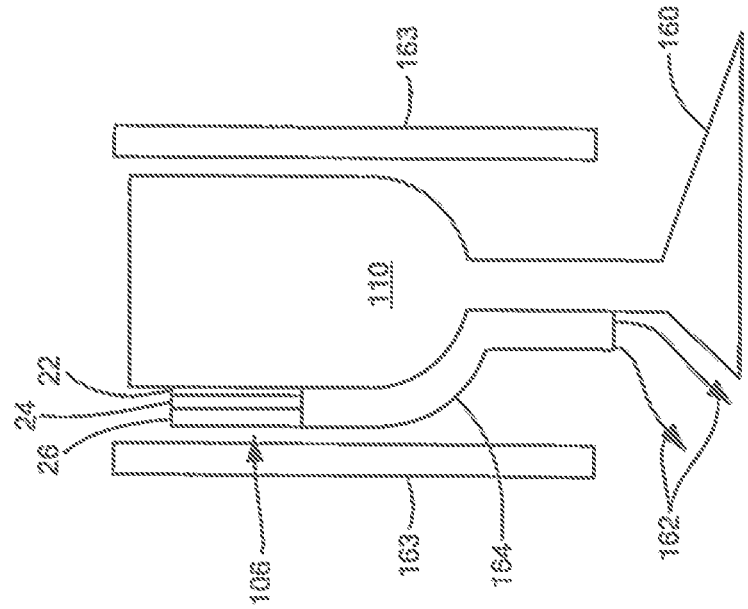
FIG. 24 is a schematic end-view showing one example of the fan of the heat extraction subsystem of the prosthetic socket cooling system shown in one or more of FIGS. 15-23C configured to direct air in a downward direction from the prosthetic socket towards the foot of a user.
Figure 25:
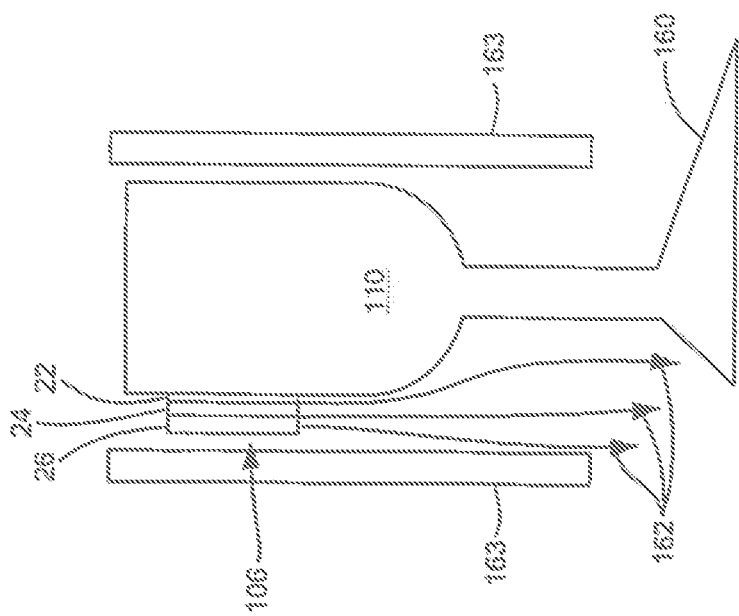
FIG. 25 is a schematic end-view showing one example of flexible bellows coupled to the heat extraction subsystem shown in FIG. 24.

In one design, fan 26, FIG. 24, of heat extraction subsystem 106 is preferably configured to urge air in a downward direction from prosthetic socket 110 towards foot 160 of a user, e.g., in the direction indicated by arrows 162. In one example, system 100 may include flexible bellows 164, FIG. 25, coupled to fan 26 configured to direct the air in the downward direction from prosthetic socket 110 towards foot 160 of the user, e.g., in the direction indicated by arrows 162.

Figure 26:
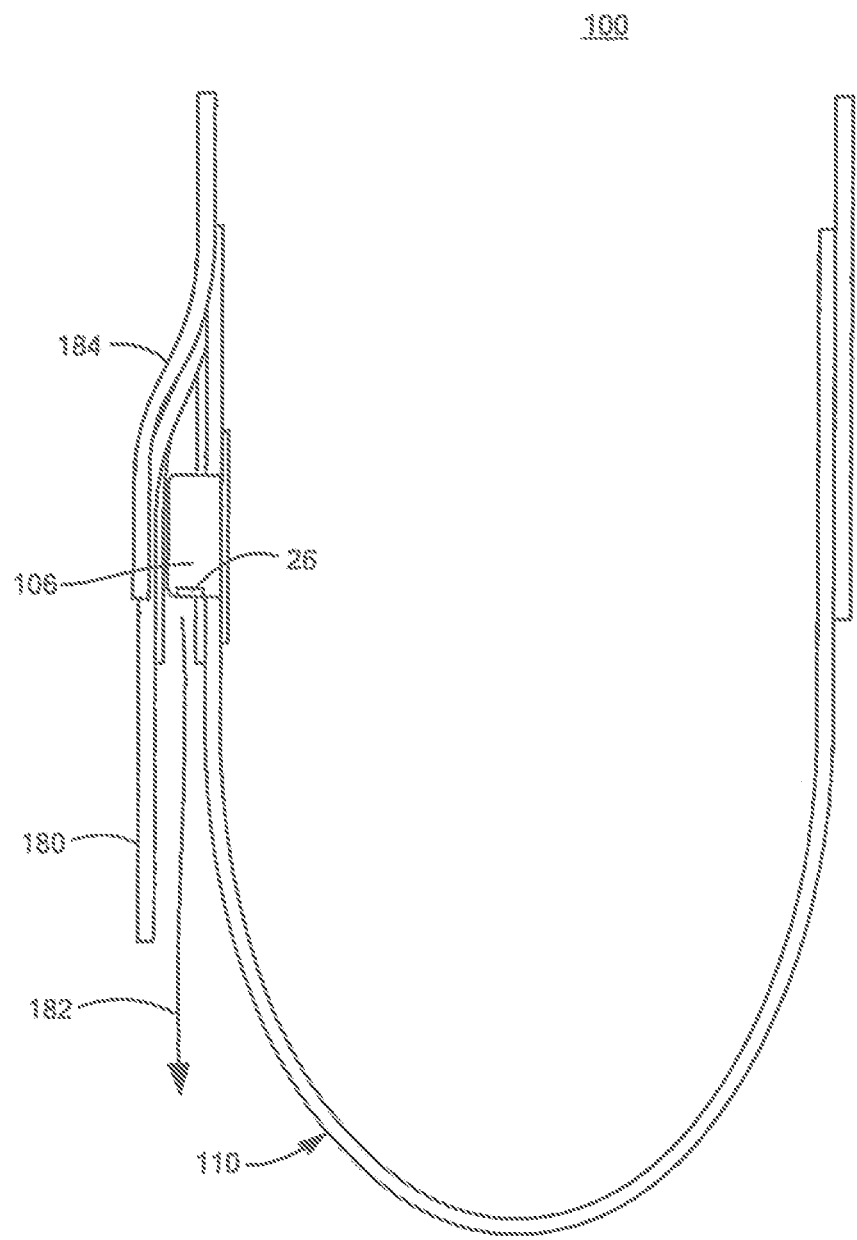
FIG. 26 is a schematic side-view showing one example of a fan coupled to a prosthetic socket configured to allow the heat extraction subsystem to direct air in a downward direction from the prosthetic socket towards the foot of a user when a suspension sleeve is placed over the prosthetic socket and the residual limb of a user.
Figure 27:
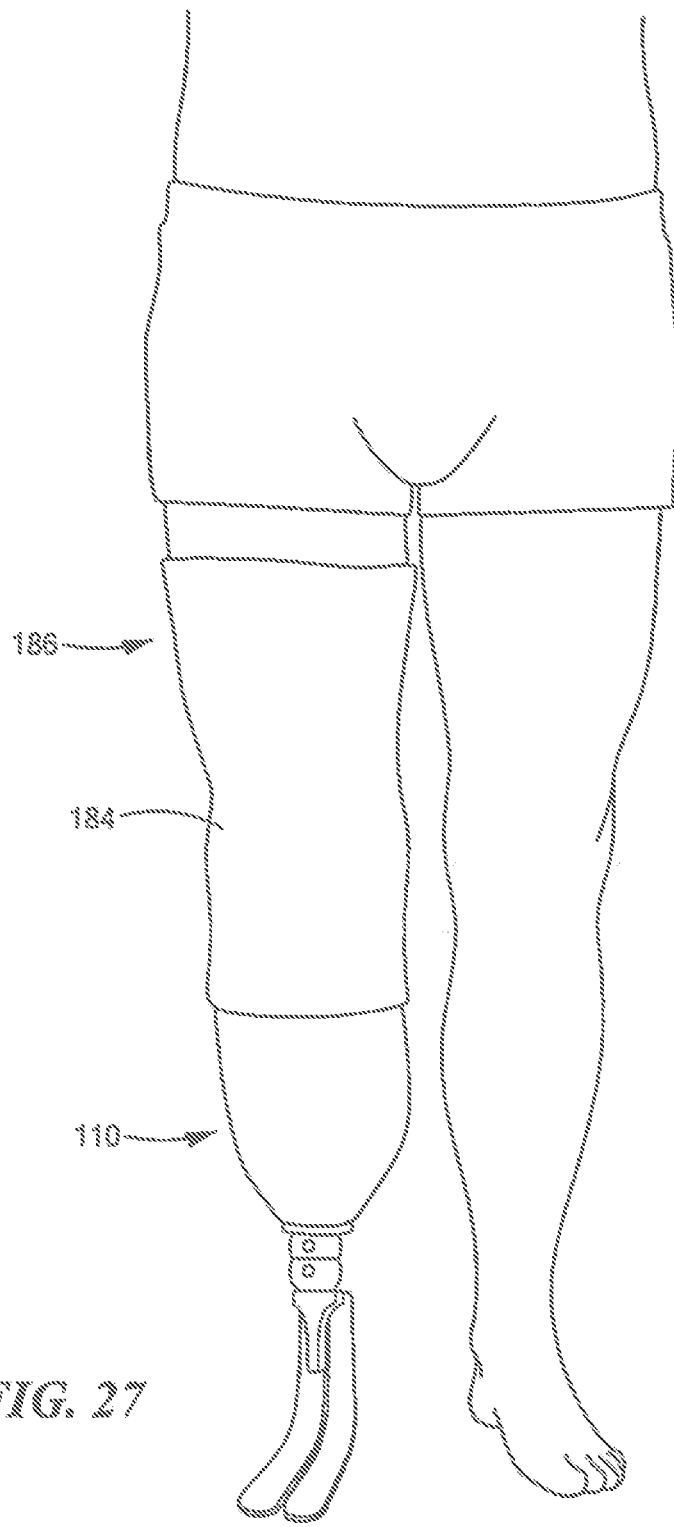
FIG. 27 is a three-dimensional view showing an example of a suspension sleeve in place over a residual limb of a user and a prosthetic socket.
Figure 28:
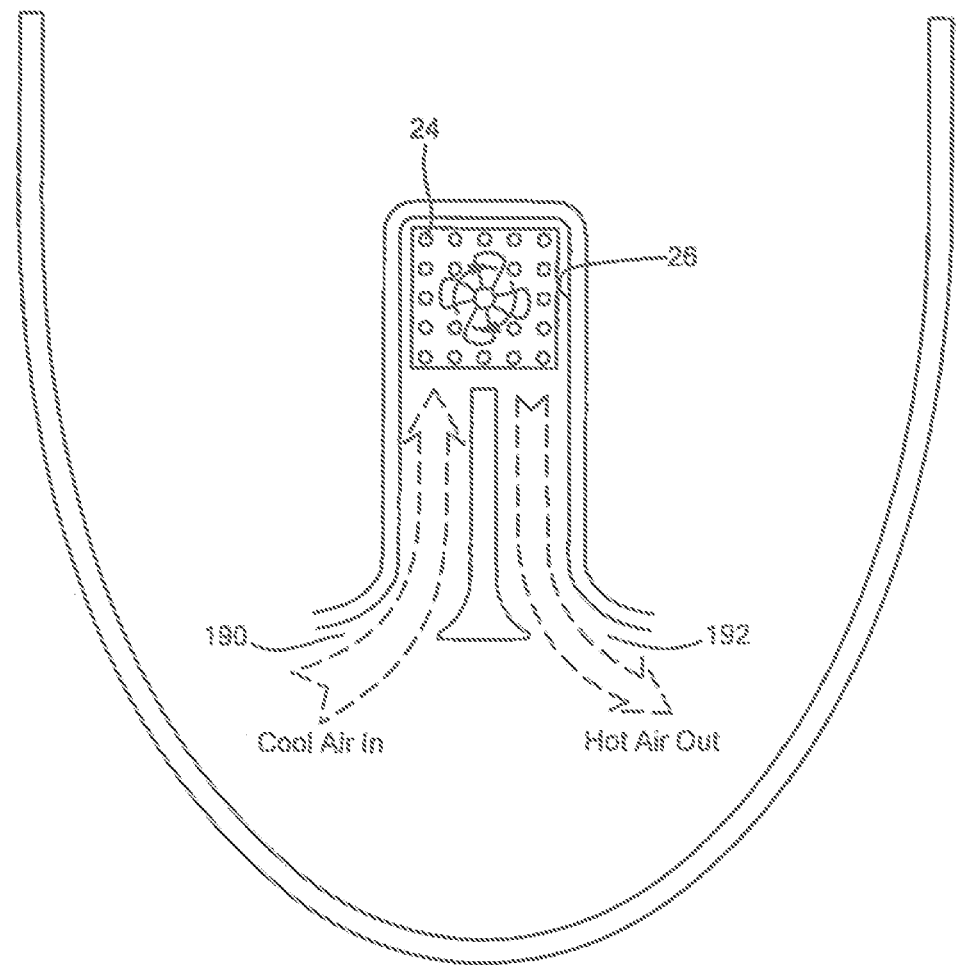
FIG. 28 is a schematic end-views showing in further detail one example of the flow of air into and out of the fan of the heat extraction subsystem shown in FIG. 26.

System 100 may include protective housing 180, FIG. 26, which may be coupled to prosthetic socket 110 as shown or to heat extraction subsystem 106. Protective housing 180 preferably allows fan 26 of heat extraction subsystem 106 to direct air in downward direction 182 when suspension sleeve 184 is placed over residual limb 186, FIG. 27, and prosthetic socket 110 as shown. Protective housing 180, FIG. 26, also prevents suspension sleeve 184 from contacting heat extraction subsystem 106 as shown. FIG. 28 shows in further detail one example of inlet port 190 and outlet port 192 configured to allow the flow of cool air into fan 26 and expel warmed or hot air via port 192 as shown.

Figure 29:
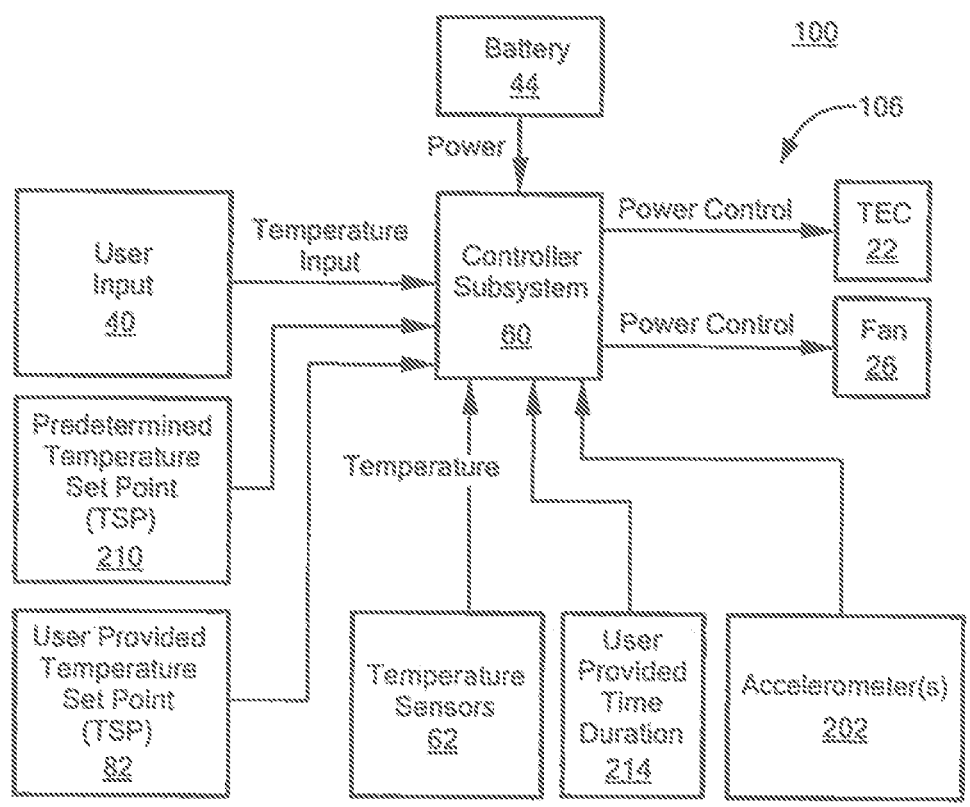
FIG. 29 is a block diagram showing the primary components associated with a prosthetic socket cooling system shown in one or more of FIGS. 10-28.
Figure 30:
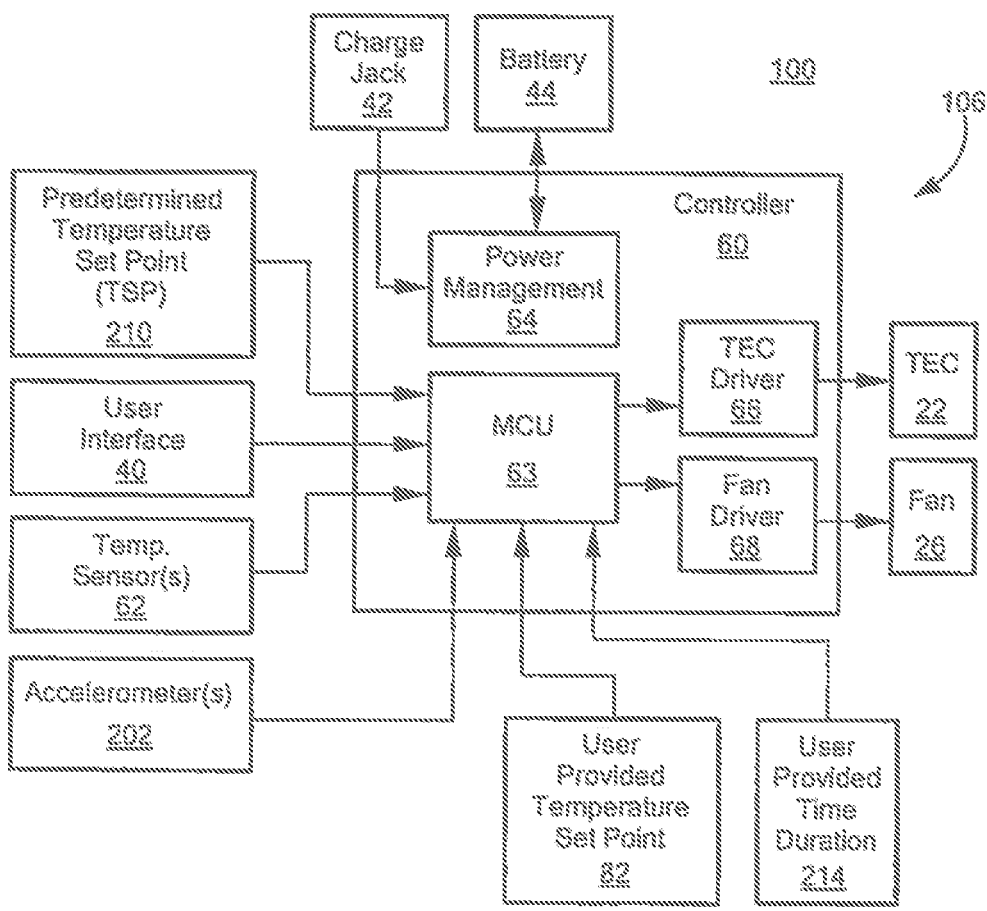
FIG. 30 is another block diagram showing additional details associated with an example of a prosthetic socket cooling system shown in one or more of FIGS. 10-28.

Prosthetic socket cooling system 100, shown in one or more of FIGS. 15-28, and the method thereof preferably includes include controller subsystem 60, FIGS. 15, 29, and 30, configured to operate heat extraction subsystem 106 to provide the desired temperature inside prosthetic socket 110, similar to heat extraction subsystem device 20 discussed above with reference to one or more of FIGS. 1-14. System 100, FIGS. 15-30, and the method thereof preferably provides the desired temperature inside prosthetic socket 110, based on information as provided by one of more of user input 40, FIG. 29, and information from one or more temperature sensors 62, FIG. 15, preferably placed in or on prosthetic socket 110 preferably near residual limb 105, the hot-side of TEC 22, the cold-side of TEC 22, the skin of residual limb 105, and/or any location between the cold-side of the TEC 22 and the skin of the residual limb 105, thermally conductive heat spreader 102, ambient air 213, thermally conductive adapter 120, thermally conductive adapter 152, thermally conductive spacer 178, heat sink 24, and/or one or more accelerometers 202, typically placed in or on prosthetic socket near residual limb 105, and each preferably coupled to controller subsystem 60.

Similar as discussed above with reference to one or more of FIGS. 10-14, controller subsystem 60, FIG. 29, and MCU 63, FIG. 30, may be programmed such that system 100 provides the desired temperature, inside prosthetic socket 110, e.g., about 50° F. to about 95° F., within prosthetic socket 16, FIG. 15.

In one example, e.g., the Mode A Cooling Control Loop discussed above with reference to FIGS. 13A and 13B, one or more temperature sensors 62, FIGS. 15, 29, and 30 are configured to measure and/or estimate one or more of the skin temperature of residual limb 105, temperature of the hot-side of TEC 22, the temperature of the cold-side of TEC 22, and/or any location between the cold-side of the TEC 22 and the skin of the residual limb 105, and controller subsystem 60 adjusts the cooling temperature of TEC 22 based on one of more of the measured and/or estimated skin temperature, the temperature of the hot-side of TEC 22 and the temperature of the cold-side of TEC 22, and TSP 82, FIGS. 29 and 30, as discussed above with reference to FIG. 13A, or predetermined set point 210, discussed above with reference to FIG. 13B, such that a desired temperature is maintained inside prosthetic socket, in the range of about 50° F. to about 95° F.

In another example, the Mode B Cooling Control Loop discussed above with reference to FIGS. 13C and 13D, one or more temperature sensors 62, FIGS. 15, 29, and 30, are preferably configured to measure and/or estimate the one or more of: the skin temperature of residual limb 105, the temperature of the hot-side of TEC 22, the temperature of the cold-side of TEC 22, or any location between the cold-side of TEC 22 and the skin of residual limb 105, ambient air 213 temperature. One or more accelerometers 202, FIGS. 29 and 30, are preferably configured to determine motion activity of a user of system 100. Controller subsystem 60 is preferably configured to adjust the temperature of TEC 22 such that a desired temperature is maintained inside prosthetic socket 100 by heat extraction subsystem 106 based on one or more of the measured and/or estimated skin temperature, the temperature of the hot-side of TEC 22 the temperature of the cold-side of the TEC, the ambient air temperature, the motion activity, and TSP 82 discussed above with reference to FIG. 13C or the predetermined set point 210, FIGS. 29 and 30 discussed above with reference to FIG. 13D such that a desired temperature is maintained inside prosthetic socket 100, e.g., in the range of about 50° F. to about 95° F.

In one design, the Mode C Cooling Control Loop discussed above with reference to FIGS. 13E and 13F, controller subsystem 60, is preferably configured to activate TEC 22 for a first predetermined duration of time, e.g., about 10 or 20 minutes, or similar amount of time and not activate TEC 22 for a second predetermined duration of time, e.g., about 1 or 5 minutes, or similar amount of time provided by user provided time duration set point 214, in prosthetic socket 110, and TSP 82 discussed above with reference to FIG. 13E, or predetermined set point 210, discussed above with reference to FIG. 13F, such that a desired temperature inside prosthetic socket 110 is maintained, e.g., in in the range of about 50° F. to about 95° F.

Figure 31:
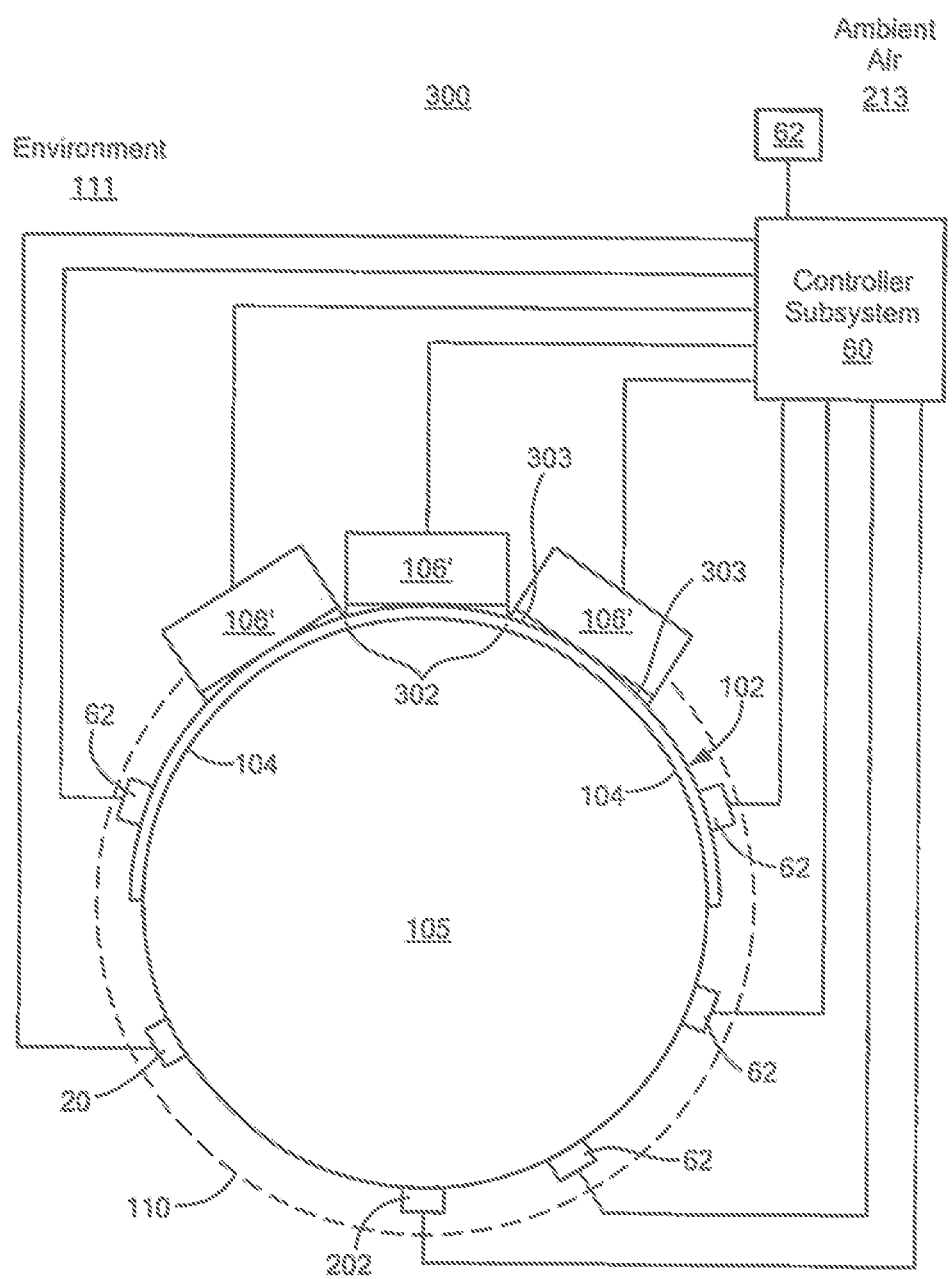
FIG. 31 is a schematic end-view of another example of the prosthetic cooling system.

In another design, system 300, FIG. 31, preferably includes thermally conductive heat spreader 102 with curved shaped portion similar as discussed above with reference to one or more of FIGS. 15-30. In this example, system 300 includes a plurality of heat extraction subsystems 106' coupled through wall 108 of prosthetic socket 110. Each of heat extraction subsystems 106' preferably have a small size configured to maximize contact with thermally conductive heat spreader 102, e.g., about 10 mm in width and about 20 mm thick, or similar small size. Each of the small sized heat extraction subsystems 106' preferably include one or more of a small sized TEC 22, heat sink 24 and fan 26 of similar design as discussed above with reference to one or more of FIGS. 15-30, e.g., about 10 mm in width and about 20 mm thick, or similar small size, and operate in a similar manner. In this example, multiple heat extraction subsystems 106' are preferably used instead of one large heat extraction subsystems 106 to allow for small joints 302 to be created between each of heat extraction subsystems 106' to allow thermally conductive heat spreader 102 and heat extraction subsystems 106' to conform to the shape of residual limb 105. In one example, a thermal adhesive may be utilized to provide smaller air gaps 303 between each of TECs 302 and thermally conductive heat spreader 102 as shown. The plurality of small sized heat extraction subsystems increase the cooling capacity of system 300. System 300 and the method thereof also preferably includes controller subsystem 60, one more temperature sensors 62, and/or one or more accelerometers 202 operates similar to system 100 discussed above with reference to one or more of FIGS. 16-30 to maintain a desired temperature inside prosthetic socket 110.

The result is prosthetic cooling system 100 with thermally conductive heat spreader 102 including curved shaped portion 104 which conforms to the shape of the residual limb provides universal fit such that system 100 efficiently transfers heat from the thermally conductive heat spreader to the thermally conductive adapter and then to the heat extraction subsystem 106. The controller subsystem coupled to one or more temperature sensors which measure one or more of the IST, the skin temperature of the residual limb, the temperature of the hot-side of the TEC, the temperature of the cold-side of the TEC, or the temperature at any location between the skin of the residual limb and the cold-side of the TEC, and ambient air temperature and one or more accelerometers which measure motion activity preferably uses the Modes A, B, and/or C Cooling Control Loop algorithms to effectively and efficiently maintains a desired temperature inside the prosthetic socket to reduce or eliminate the problems associated with increased prosthetic socket temperature discussed in the Background section above.

The following Exemplary Code is provided which can be executed by Controller subsystem and/or the MCU to carry out the calculations, steps and/or functions discussed above. Other equivalent algorithms and code can be designed by a software engineer and/or programmer skilled in the art using the information provided therein:

```
Exemplary Code:
Main Control Loop Pseudocode:
void function main
{
    Call system_Check, and retrieve the TRUE/FALSE result
    Set the value of system_normal equal to the TRUE/FALSE result
    if the value of system_normal is equal to TRUE
        Call Cooling_Control_Loop
    if the value of system_normal is equal to FALSE
        Call system_Error
    if the power button is pressed
        Call system OFF
}
boolean function system_Check
{
    read all temperature sensors
    read battery level
    if the value of the temperature_sensors is within the correct range
        AND   the battery level is within the correct range
        return TRUE
    else
        return FALSE
}
void function system_Error
{
    Enable error indicator
    Wait for several seconds
    Call system_OFF
}
void function system_OFF
{
    Turn Cooling System OFF
    Turn Controller OFF
}
```

Mode A Cooling Control Loop Pseudocode (TEC and Fan):
COMMENT: This control mode regulates temperature based on intra-socket temperature sensors and TEC temperature difference
void function Cooling_Control_Loop
{
  Call get_Temperature_Error, retrieve the decimal number result
  Set the value of temperature_Error equal to the decimal number result
  Call get_TEC_Temperature_Difference, retrieve the decimal number result
  Set the value of TEC_Temperature_Difference equal to the decimal number result
  Call compute_FAN_OUTPUT, provide the temperature_Error and TEC_Temperature_Difference, and retrieve the result
  Set the value of FAN_Control equal to the decimal number result
  Send the value of FAN_Control to the FAN driver
  Call compute_TEC_OUTPUT, provide the temperature_Error and TEC_Temperature_Difference, and retrieve the result
  Set the value of TEC_Control equal to the decimal number result
  Send the value of TEC_Control to the TEC driver
}
decimal function get_Temperature_Error
{
  read the temperature set point
  Call get_Intra-Socket_Temperature, retrieve the decimal number result
  temperature_Error is set equal to (temperature set point) minus (Intra-socket temperature)
  return temperature_Error
}
COMMENT: When user provided temperature set point provided, change "temperature set point" to "user provided temperature set point"
decimal function get_Intra-Socket_Temperature
{
COMMENT: This function computes a weighted average of the value of the intra-socket temperature sensors using predetermined weights 
  read the Number_of_Intra-Socket_sensors and save as NSENS
  read the predetermined decimal weights for each Intra-Socket sensor,
  Let decimal variable SUM = 0
  Let decimal variable WSUM = 0
  LOOP over j, from j=1 to j= NSENS {
  BEGIN LOOP
      Read the temperature value from Intra-Socket Sensor Number j and save as Tj
      read the predetermined decimal weight for Intra-Socket sensor j and save as WEIGHT
      Multiply Tj by WEIGHT and add the result to SUM
      Add WEIGHT to WSUM.
  END LOOP }
  Intra-Socket_Temperature is set equal to (SUM divided by NSENS) divided by WSUM
  return Intra-Socket_Temperature
}
decimal function get_TEC_Temperature_Difference
{
  read the temperatures of the HOT and COLD-side of the TEC
  TEC_Temperature_Difference is set equal to (HOT-side temperature) minus (COLD-side temperature)
  return TEC_Temperature_Difference
}
decimal function compute_TEC_OUTPUT(temperature_Error, TEC_Temperature_Difference)
{
TEC_Output is set equal to the result of a transfer function T(s), that computes a value given temperature_Error and TEC_Temperature_Difference
 return TEC_Output
}
decimal function compute_FAN_OUTPUT(temperature_Error, TEC_Temperature_Difference);
{
   FAN Output is set equal to the result of a transfer function F(s), that computes a value given temperature_Error and TEC_Temperature_Difference
return FAN_Output
}
Mode B Cooling Control Loop Pseudocode (TEC and Fan):
COMMENT: This control mode regulates temperature based on intra-socket temperature, ambient temperature, motion activity and TEC temperature difference
void function Cooling_Control_Loop
{
  Call get_Temperature_Error, retrieve the decimal number result
  Set the value of temperature_Error equal to the decimal number result
  Call get_TEC_Temperature_Difference, retrieve the decimal number result
  Set the value of TEC_Temperature_Difference equal to the decimal number result
  Read ambient temperature and store as Ambient_Temp
  Read motion_activity level from the accelerometer and store as Motion_Activity
  Call compute_FAN_OUTPUT, provide the temperature_Error and TEC_Temperature_Difference, and retrieve the result
  Set the value of FAN_Control equal to the decimal number result
  Send the value of FAN_Control to the FAN driver

```
   Call compute_TEC_OUTPUT, provide the temperature_Error and TEC_Temperature_Difference,
and retrieve the result
   Set the value of TEC_Control equal to the decimal number result
   Send the value of TEC_Control to the TEC driver
}
decimal function get_Temperature_Error
{
   read the temperature set point
   Call get_Intra-Socket_Temperature, retrieve the decimal number result
   temperature_Error is set equal to (temperature set point) minus (Intra-socket temperature)
   return temperature_Error
}
COMMENT: **When user provided temperature set point provided, change "temperature set point" to
"user provided temperature set point"**
decimal function get_Intra-Socket_Temperature
{
** This function computes a weighted average of the value of the intra-socket temperature sensors
using
predetermined weights **
   read the Number_of_Intra-Socket_sensors and save as NSENS
   read the predetermined decimal weights for each Intra-Socket sensor,
   Let decimal variable SUM = 0
   Let decimal variable WSUM = 0
   LOOP over j, from j=1 to j= NSENS {
   BEGIN LOOP
       Read the temperature value from Intra-Socket Sensor Number j and save as Tj
       read the predetermined decimal weight for Intra-Socket sensor j and save as WEIGHT
       Multiply Tj by WEIGHT and add the result to SUM
       Add WEIGHT to WSUM.
   END LOOP }
   Intra-Socket_Temperature is set equal to (SUM divided by NSENS) divided by WSUM
   return Intra-Socket_Temperature
}
decimal function get_TEC_Temperature_Difference
{
   read the temperatures of the HOT and COLD-side of the TEC
   TEC_Temperature_Difference is set equal to (HOT-side temperature) minus (COLD-side
temperature)
   return TEC_Temperature_Difference
}
decimal function compute_TEC_OUTPUT(temperature_Error, TEC_Temperature_Difference)
{
TEC_Output is set equal to the result of a transfer function T(s), that computes a value given:
temperature_Error, Ambient_Temp, Motion_Activity and TEC_Temperature_Difference
 return TEC_Output
}
decimal function compute_FAN_OUTPUT(temperature_Error, TEC_Temperature_Difference);
{
    FAN Output is set equal to the result of a transfer function F(s), that computes a value given
temperature_Error and TEC_Temperature_Difference
 return FAN_Output
}
Mode C Cooling Control Loop Pseudocode (TEC and Fan):
COMMENT: **This control mode regulates temperature by turning cooling on for a first predetermined
duration of time, then off for a second predetermined duration of time , then repeating**
void function Cooling_Control_Loop
{
   Read system timer and save as Current_Time
   Set GLOBAL decimal variable Start_Time equal to Current_Time
   Set decimal variable Elapsed_Time equal to zero (0)
   LOOP FOREVER {
       Read system timer and save as Current_Time
       Set decimal variable Elapsed_Time equal to Current_time minus Start_Time
       Read the first predetermined duration of time, and save as On_Time
       Read the second predetermined duration of time and save as Off_Time
       Set decimal variable Cycle_Time equal to On_Time plus Off_Time
       Set Time_In_Cycle = Elapsed_time MOD Cycle Time
           (i.e., Remainder after Elapsed_Time divided by Cycle_Time)
       IF ( Time_In_Cycle < On_Time ) {
          Set Binary variable MODE = ON
       ELSE
          Set Binary variable MODE = OFF
       Call get_Temperature_Error, retrieve the decimal number result, save as
Temperature_Error
       Call get_TEC_Temperature_Difference, retrieve the decimal number result,
          save as TEC_Temperature_Difference
       Read temperature set point, and save as T_Desired
       Call compute_TEC_OUTPUT, provide the MODE, On_Time, Off_Time,
```

```
Temperature_Error, and
        TEC_Temperature_Difference, and retrieve the result
        Set the value of TEC_Control equal to the decimal number result
        Send the value of TEC_Control to the TEC driver
    END LOOP FOREVER }
}
COMMENT: **When user provided temperature set point provided, change "temperature set point" to
"user provided temperature set point"**
decimal function compute_TEC_OUTPUT( On_Time, Off_Time, Temperature_Error,
TEC_Temperature_Difference)
{
    IF (MODE == ON {
        TEC_Output is set equal to the result of a transfer function T(s), that computes a value
    given:
        On_Time, Off_Time, Temperature_Error, and TEC_Temperature_Difference,
    }
    ELSE {
        TEC_Output = Zero (0)
    }
    return TEC_Output
}
decimal function compute_FAN_OUTPUT(temperature_Error, TEC_Temperature_Difference);
{
    FAN Output is set equal to the result of a transfer function F(s), that computes a value given
temperature_Error and TEC_Temperature_Difference
    return FAN_Output
}
```

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

What is claimed is:

1. A prosthetic socket cooling system comprising:
a thermally conductive heat spreader, the entire thermally conductive heat spreader adapted to be placed away from a distal end of a residual limb of a human subject and made of a single layer solid sheet of a thermally conductive material including a curved shaped portion configured to maximize contact with the outer circumference of the residual limb of a user; and
a heat extraction subsystem coupled through a wall of the prosthetic socket and to the thermally conductive heat spreader configured to maintain a desired temperature inside the prosthetic socket.

2. The system of claim 1 in which the thermally conductive heat spreader and the heat extraction subsystem are positioned at a mid-location of the prosthetic socket.

3. The system of claim 1 in which the thermally conductive heat spreader and the heat extraction subsystem are positioned at an upper-location of the prosthetic socket.

4. The system of claim 1 in which the heat extraction subsystem includes a thermal electric cooler (TEC) having a predetermined shape and a flat surface having a predetermined surface area.

5. The system of claim 4 in which the heat extraction subsystem includes a heat sink coupled to the TEC and a fan positioned to urge air over the heat sink.

6. The system of claim 5 in which the fan is configured to urge the air in a downward direction from the prosthetic socket towards a foot of the user.

7. The system of claim 6 further including a conduit coupled to the fan configured to direct the air in the downward direction.

8. The system of claim 7 further including flexible bellows coupled to the fan configured to direct the air in a downward direction.

9. The system of claim 6 further including a protective housing coupled to the prosthetic socket configured to allow the fan to direct the air in the downward direction when a suspension sleeve placed over the residual limb and the prosthetic socket.

10. The system of claim 4 further including a thermally conductive adapter coupled between the thermally conductive heat spreader and the heat extraction subsystem.

11. The system of claim 10 in which the thermally conductive adapter includes a curved surface on one side configured to approximately match the curved shaped portion of the thermally conductive heat spreader and a flat surface on the other side configured to approximately match the flat surface and predetermined surface area of the TEC.

12. The system of claim 10 in which the thermally conductive heat spreader includes a flat portion.

13. The system of claim 12 in which the thermally conductive adapter includes a flat surface on one side configured to approximately match the flat portion of the thermally conductive heat spreader and a flat surface on the other side and configured to approximately match the predetermined shape, flat surface, and predetermined surface area of the TEC.

14. The system of claim 13 in which the flat surface on the side configured to approximately match the flat portion of the thermally conductive heat spreader is sized to conform to the residual limb of the user.

15. The system of claim 10 further including a thermally conductive spacer coupled between the thermally conductive adapter and the TEC.

16. The system of claim 4 in which the thermally conductive heat spreader is sized to maximize performance of the TEC.

17. The system of claim 5 in which the heat extraction subsystem further includes a user interface, an electronic section, one or more temperature sensors, one or more accelerometers, and a power supply.

18. The system of claim 17 further including a housing about the fan, the TEC, the heat sink, the user interface, the electronics section, and the battery.

19. The system of claim 18 in which the electronics section further includes a controller subsystem.

20. The system of claim 19 in which the controller subsystem is configured to operate the TEC based and/or the fan based on signals from the user interface and/or the one or more temperature sensors and/or the one or more accelerometers.

21. The system of claim 20 in which the controller subsystem and the one or more temperature sensors are configured to measure and/or estimate skin temperature of the residual limb of the user and adjust a cooling temperature of the TEC based on the measured or estimated skin temperature and a predetermined set point temperature.

22. The system of claim 20 in which one or more of the controller subsystem, the one or more temperature sensors, or the one or more accelerometers are configured to measure or estimate one of more of: a skin temperature of the residual limb of the user, a temperature of a hot-side of the TEC, a temperature of a cold-side of the TEC, an ambient temperature, or motion activity of the user and the controller subsystem is configured to adjust the temperature of the TEC such that a desired temperature is maintained inside the prosthetic socket based on one or more of the measured and/or estimated skin temperature, the temperature of the hot-side of the TEC, the temperature of the cold-side of the TEC, the ambient temperature, the motion activity, and a predetermined set point temperature.

23. The system of claim 20 in which the controller subsystem is configured to adjust the temperature of the TEC such that a desired temperature inside the prosthetic socket is maintained based on a temperature set point provided by the user.

24. The system of claim 20 in which one or more of the controller subsystem, the one or more temperature sensors, and the one or more accelerometers are configured to measure or estimate one or more of: a skin temperature of the residual limb of the user, a temperature of a hot-side of the TEC, a temperature of a cold-side of the TEC, an ambient temperature, or motion activity of the user and the controller subsystem is configured to adjust the temperature the TEC such that a desired temperature inside the prosthetic socket is maintained based on one or more of the measured and/or estimated skin temperature, the temperature of the hot-side and the cold-side of the TEC, the ambient temperature, the motion activity, and a temperature set point provided by the user.

25. The system of claim 20 in which the controller subsystem is configured to activate the TEC for a first predetermined duration of time and not activate the TEC for a second predetermined duration of time based on a set point provided by the user such that the desired temperature inside the prosthetic socket is maintained.

26. The system of claim 20 in which one or more of the controller subsystem, the one or more temperature sensors, or the one or more accelerometers are configured to determine one or more of: an ambient temperature, a temperature of a hot-side of the TEC, a temperature of a cold-side of the TEC, or motion activity of the user and the controller subsystem is configured to activate the TEC for a first predetermined duration of time and not activate the TEC for a second predetermined duration of time based on a set point provided by the user such that the desired temperature inside the prosthetic socket is maintained.

27. A prosthetic socket cooling system comprising:
a thermally conductive heat spreader, the entire thermally conductive heat spreader adapted to be placed away from a distal end of a residual limb of a human subject and made of a single layer solid sheet of a thermally conductive material including a curved shaped portion configured to maximize contact a residual limb of a user; and
a plurality of heat extraction subsystems coupled through a wall of the prosthetic socket and to the thermally conductive heat spreader, the plurality of heat extraction subsystems are sized to maximize contact with thermally conductive heat spreader.

28. The system of claim 27 in which the thermally conductive heat spreader and the plurality of heat extraction subsystems are positioned at a mid-location of the prosthetic socket.

29. The system of claim 27 in which the thermally conductive heat spreader and the plurality of heat extraction subsystems are positioned at an upper-location of the prosthetic socket.

30. The system of claim 27 in which each of the plurality of heat extraction subsystems include a thermal electric cooler (TEC).

31. The system of claim 30 in which each of the plurality of the heat extraction subsystems includes a heat sink coupled to the TEC and a fan positioned to urge air over the heat sink.

32. The system of claim 31 further including one or more of: a user interface, an electronic section, one or more temperature sensors, one or more accelerometers, and a power supply.

33. The system of claim 32 in which the electronics section further includes a controller subsystem.

34. The system of claim 33 in which the controller subsystem is configured to operate each TEC and/or the fan based on signals from the user interface and/or the one or more temperature sensors and/or the one or more accelerometers.

35. The system of claim 34 in which the controller subsystem and the one or more temperature sensors are configured to measure and/or estimate one or more of: a skin temperature of the residual limb of the use, a temperature of a hot-side of the TEC, the temperature of a cold-side of the TEC, and adjust a cooling temperature of the TEC based on one or more of the measured and/or estimated skin temperature, the temperature of the hot-side and the TEC, a temperature of a cold-side of the TEC, or a predetermined set point temperature.

36. The system of claim 34 in which the controller subsystem, the one or more temperature sensors, and/or the one or more accelerometers are configured to measure and/or estimate one or more of: a temperature of skin of the residual limb of the user, a temperature of a hot-side of the TEC, a temperature of a cold-side of the TEC, an ambient temperature, and motion activity of the user and the controller subsystem is configured to adjust the temperature of the TEC such that a desired temperature is maintained inside the prosthetic socket based on one or more of the measured and/or estimated skin temperature, the temperature of the hot-side of the TEC, the temperature of the cold-side of the TEC, the ambient temperature, the motion activity, or a predetermined set point temperature.

37. The system of claim 34 in which the controller subsystem is configured to adjust the temperature of the TEC such that the desired temperature inside the prosthetic socket is maintained based on a temperature set point provided by the user.

38. The system of claim 34 in which the controller subsystem, the one or more temperature sensors, and the one or more accelerometers are configured to measure and/or estimate one or more of: a skin temperature of the residual limb of the user, a temperature of a hot-side of the TEC, a temperature of a cold-side of the TEC, an ambient temperature, and motion activity of the user and the controller subsystem is configured to adjust the temperature the TEC such that the desired temperature inside the prosthetic socket is maintained based on one or more of the measured and/or estimated skin temperature, the temperature of the hot-side and the cold-side of the TEC, the ambient temperature, the motion activity, or a temperature set point provided by the user.

39. A method of cooling a prosthetic socket, the method comprising:
  placing a thermally conductive heat spreader including a curved shape portion in contact with a residual limb of a user, away from a distal end of the residual limb;
  the thermally conductive heat spreader made of a single layer of solid sheet of a thermally conductive material;
  placing a heat extraction subsystem through a wall of the prosthetic socket and coupling the heat extraction subsystem to the thermally conductive heat spreader;
  and operating the heat extraction subsystem to drive heat from inside the prosthetic socket to an external environment using the thermally conductive heat spreader and the heat extraction subsystem such that a desired temperature is maintained in the prosthetic socket.

40. The method of claim 39 further including placing the thermally conductive heat spreader and the heat extraction subsystem at a mid-location of the prosthetic socket.

41. The method of claim 39 further including placing the thermally conductive heat spreader and the heat extraction subsystem at an upper-location of the prosthetic socket.

42. The method of claim 39 further including coupling a thermally conductive adapter between the thermally conductive heat spreader and the heat extraction subsystem.

43. The method of claim 39 further including urging air in a downward direction from the prosthetic socket towards a foot of the user.

44. The method of claim 39 in which the heat extraction subsystem further includes one or more of: a thermoelectric cooler (TEC), a user interface, an electronic section, one or more temperature sensors, one or more accelerometers, a fan, a heat sink, or a power supply.

45. The method of claim 44 further including operating the TEC and/or the fan based on signals from the user interface and/or the one or more temperature sensors and/or the one or more accelerometers.

46. The method of claim 45 further including using a controller subsystem and the temperature sensors for measuring and/or estimating one or more of:
  a skin temperature of the residual limb of the user, a temperature of a hot-side of the TEC, a temperature of a cold-side of the TEC
  and adjusting a cooling temperature of the TEC based on one or more of the measured and/or estimated skin temperature, the temperature of the hot-side of the TEC, the temperature of the cold-side of the TEC, and a predetermined set point temperature.

47. The method of claim 45 further including using a controller subsystem and the temperature sensors for measuring and/or estimating one or more of:
  a skin temperature of the residual limb of the user, a temperature of a hot-side of the TEC, a temperature of a cold-side of the TEC, an ambient temperature, and/or motion activity of the user
  and adjusting the temperature the TEC such that a desired temperature is maintained inside the prosthetic socket based on one or more of the measured and/or estimated on the skin temperature, the ambient temperature, the temperature of the hot-side and the cold-side of the TEC, the motion activity, or the predetermined set point temperature.

48. The method of claim 45 further including adjusting the temperature of the TEC such that the desired temperature inside the prosthetic socket is maintained based on a temperature set point provided by the user.

49. The method of claim 45 further including using a controller subsystem and the temperature sensors for measuring and/or estimating one or more of:
  a temperature of skin of the residual limb of the user, a temperature of a hot-side of the TEC, a temperature of a cold-side of the TEC, an ambient temperature, or motion activity of the user
  and adjusting the temperature the TEC such that the desired temperature inside the prosthetic socket is maintained based on one or more of the measured or estimated skin temperature, the temperature of the hot-side of the TEC, the temperature of the cold-side of the TEC, the ambient temperature, the motion activity, and temperature set point provided by the user.

50. A method of cooling a prosthetic socket, the method comprising:
  providing a thermally conductive heat spreader including a curved shape portion in contact with a residual limb of a user,
  the entire thermally conductive heat spreader placed away from a distal end of the residual limb of a human subject;
  providing a plurality of heat extraction subsystems through a wall of the prosthetic socket and coupling the plurality of heat extraction subsystems to the thermally conductive heat spreader;
  wherein the plurality of heat extraction subsystems comprises a thermoelectric cooler (TEC);
  and operating the plurality of heat extraction subsystems to drive heat from the prosthetic socket to an external environment via the thermally conductive heat spreader and the heat extraction subsystem to maintain a desired temperature inside the TEC.

* * * * *